(12) United States Patent
Haj-Ahmad

(10) Patent No.: US 10,577,645 B2
(45) Date of Patent: Mar. 3, 2020

(54) METHODS AND KITS FOR IMPROVING GLOBAL GENE EXPRESSION ANALYSIS OF HUMAN BLOOD, PLASMA AND/OR SERUM DERIVED RNA

(71) Applicant: Norgen Biotek Corp., Thorold, Ontario (CA)

(72) Inventor: Yousef Haj-Ahmad, St. Catharines (CA)

(73) Assignee: Norgen Biotek Corp., Ontario (CA)

( * ) Notice: Subject to any disclaimer, the term of this patent is extended or adjusted under 35 U.S.C. 154(b) by 52 days.

(21) Appl. No.: 15/460,826

(22) Filed: Mar. 16, 2017

(65) Prior Publication Data

US 2017/0268040 A1 Sep. 21, 2017

Related U.S. Application Data

(60) Provisional application No. 62/310,389, filed on Mar. 18, 2016.

(51) Int. Cl.
| | | |
|---|---|---|
| *C12Q 1/68* | (2018.01) | |
| *C07H 21/00* | (2006.01) | |
| *C12Q 1/6806* | (2018.01) | |
| *C12N 15/10* | (2006.01) | |
| *C12Q 1/6874* | (2018.01) | |

(52) U.S. Cl.
CPC ....... *C12Q 1/6806* (2013.01); *C12N 15/1006* (2013.01); *C12Q 1/6874* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 6,177,278 B1 | 1/2001 | Haj-Ahmad | |
| 6,291,248 B1 | 9/2001 | Haj-Ahmad | |
| 7,026,453 B2 | 4/2006 | Haj-Ahmad | |
| 7,431,842 B2 | 10/2008 | Haj-Ahmad | |
| 8,063,199 B2 | 11/2011 | Haj-Ahmad | |
| 9,422,596 B1 | 8/2016 | Haj-Ahmad | |
| 9,957,571 B2* | 5/2018 | Verrant | C12Q 1/34 |
| 2010/0029498 A1* | 2/2010 | Gnirke | C12Q 1/6869 506/9 |
| 2010/0331204 A1* | 12/2010 | Jeddeloh | C12Q 1/6806 506/9 |
| 2011/0040081 A1* | 2/2011 | Sooknanan | C12Q 1/6806 536/24.31 |
| 2012/0021407 A1 | 1/2012 | Haj-Ahmad | |
| 2013/0149705 A1* | 6/2013 | Aurich-Costa | C12Q 1/6841 435/6.11 |
| 2014/0255271 A1 | 9/2014 | Haj-Ahmad | |
| 2015/0218620 A1 | 8/2015 | Behlke et al. | |
| 2015/0275267 A1 | 10/2015 | O'Neil et al. | |
| 2016/0024575 A1* | 1/2016 | Spindler | C12Q 1/6886 506/2 |
| 2016/0326512 A1 | 11/2016 | Haj-Ahmad | |
| 2017/0101676 A1* | 4/2017 | Teng | C12Q 1/6806 |

FOREIGN PATENT DOCUMENTS

| | | | |
|---|---|---|---|
| CA | 2517770 | 2/2007 | |
| WO | WO-2011019993 A2 * | 2/2011 | ........... C12Q 1/6806 |

OTHER PUBLICATIONS

Archer et al., Selective and flexible depletion of problematic sequences from RNA-seq libraries at the cDNA stage. BMC Genomics 15 :401 (Year: 2014).*
Fu et al., Identification of human fetal liver miRNAs by a novel method. FEBS Letters 579 :3849 (Year: 2005).*
Morlan et al., Selective Depletion of rRNA Enables Whole Transcriptome Profiling of Archival Fixed Tissue. PLOS ONE 7:(8) : e42882 (Year: 2012).*
Brenu EW, Ashton KJ, Batovska J, Staines DR, Marshall-Gradisnik SM. "High-throughput sequencing of plasma microRNA in chronic fatigue syndrome/myalgic encephalomyelitis". PLoS One. Sep. 19, 2014; 9(9):e102783.
Dhahbi JM, Spindler SR, Atamna H, Boffelli D, Mote P, Martin DI. "5'-YRNA fragments derived by processing of transcripts from specific YRNA genes and pseudogenes are abundant in human serum and plasma". Physiol Genomics. Nov. 1, 2013;45(21):990-8.
Song L, Lin C, Gong H, Wang C, Liu L, Wu J, Tao S, Hu B, Cheng SY, Li M, and Li J. "miR-486 sustains NF-κB activity by disrupting multiple NF-κB-negative feedback loops". Cell Research. Dec. 18, 2012; 23:274-289.
Chen H, Ren C, Han C, Wang D, Chen Y, and Fu D. "Expression and Prognostic Value of miR-486-5p in Patients with Gastric Adenocarcinoma." PLoS One. Mar. 20, 2015; 10(3): e0119384.
Tonge DP and Gant TW. "What is normal? Next generation sequencing-driven analysis of the human circulating miRNAome." BMC Molecular Biology. Feb. 9, 2016; 17:4.
NCBI Reference Sequence: NR_004393.1.
MiRBase Accession No. MIMAT0002177.

* cited by examiner

*Primary Examiner* — Ethan C Whisenant
(74) *Attorney, Agent, or Firm* — Coats & Bennett PLLC

(57) ABSTRACT

Disclosed are methods and kits for improving global gene expression analysis for a population of RNA molecules derived from a human blood, plasma and/or serum sample. In an embodiment, the method comprises the step of selectively depleting 5'-RNAY4 fragments from the population of RNA molecules or selectively blocking 5'-RNAY4 fragments within the RNA population. The 5'-RNAY4 depleted or 5'-RNAY4 blocked population of RNA can be used in a variety of global gene expression analysis protocols, including next generation sequencing. In a further embodiment, the method comprises selectively depleting or blocking miR-486-5p fragments within the RNA population. The miR-486-5p depleted or miR-486-5p blocked population of RNA can also be used in global gene expression analysis protocols, including next generation sequencing. The kit comprises oligonucleotide probes comprising a nucleotide sequence that is the complement to a nucleotide sequence of the 5' end of the RNAY4 and/or oligonucleotide probes comprising a nucleotide sequence that is the complement to a nucleotide sequence of miR-486-5p.

4 Claims, 6 Drawing Sheets

Specification includes a Sequence Listing.

METHODS AND KITS FOR IMPROVING GLOBAL GENE EXPRESSION ANALYSIS OF HUMAN BLOOD, PLASMA AND/OR SERUM DERIVED RNA

RELATED APPLICATION

This application claims priority benefits from U.S. Provisional Patent Application No. 62/310,389 and entitled "Methods and Kits for Improving Global Gene Expression Analysis of Human Plasma and/or Serum Derived RNA", which is incorporated herein by reference in its entirety.

FIELD OF INVENTION

The present invention provides a method of improving global gene expression analysis of human blood, plasma and/or serum derived RNA, and in particular, the next generation sequencing of small RNA.

BACKGROUND

Global expression profiling of RNA and small RNA from various bodily fluids and tissue biopsies has become a staple approach for the monitoring and/or discovery of RNA biomarkers in various applications, including molecular diagnostics, dose/response effects studies, toxicity studies and other related applications. Global gene expression analysis can be carried out using a variety of methods including microarray analysis, library construction, reverse transcription, amplification, transcriptome profiling, expression analysis and sequencing, including next generation sequencing.

Human blood and more particularly, plasma and serum, contain a variety of RNA molecules, which may be medically or scientifically relevant. The relative abundances of such RNA molecules can be indicative of donor health status or responses to various endogenous and exogenous stimuli. Of the RNA molecules present in human plasma and serum, a class of small non-coding, regulatory RNAs, called microRNA (miRNA), are of particular interest as biomarkers. Interest in miRNA as biomarkers is due to both their biological role in gene expression regulation and their relative stability in circulation (as compared to larger RNA molecules, which are more readily degraded).

However, miRNA is a relatively minor constituent of the human plasma and serum small RNA milieu, mostly as result of an overwhelming abundance of another short, non-coding, RNA molecule derived from the 5' end of human RNAY4, encoded by the hY4 gene (Dhahbi et al., 2013; Brenu et al., 2014). The exact function and importance of the 5'-RNAY4 fragment has yet to be conclusively determined. Further, within the total miRNA population derived from human blood, plasma and serum, it has been found that certain miRNAs, such as miR-486-5p which has been observed to be reduced in human cancer (Song et al. 2013; Chen et al., 2015), are overrepresented.

SUMMARY OF INVENTION

Disclosed are methods of improving global gene expression analysis for a population of RNA molecules derived from human blood, plasma and/or serum. In one embodiment, the method comprises the step of depleting 5'-RNAY4 fragments and/or miR-486-5p from the population of RNA molecules. In another embodiment, the method comprises the step of blocking 5'-RNAY4 and/or miR-486-5p fragments in the population of RNA molecules. The method provides a sample, in which the 5'-RNAY4 and/or miR-486-5p fragments are preferably blocked by hybridization with complementary oligonucleotide probes. The resulting 5'-RNAY4 and/or miR-486-5p depleted or blocked population of small RNA molecules can be used in variety of downstream global gene expression analysis, and in particular, next generation sequencing.

In one aspect, disclosed is a method of improving global gene expression analysis for a population of RNA molecules derived from human blood, plasma and/or serum, the method comprising the step of depleting 5'-RNAY4 fragments and/or miR-486-5p fragments from the population of RNA molecules. The method may comprise depleting only 5'-RNAY4 fragments from the population of RNA molecules. The method may comprise depleting only miR-486-5p fragments from the population of RNA molecules. The method may comprise depleting 5'-RNAY4 and miR-486-5p fragments from the population of RNA molecules.

In an embodiment of the method, the step of depleting 5'-RNAY4 fragments from the population of RNA molecules comprises:
adding 5'-RNAY4 specific oligonucleotide probes to a sample containing the population of RNA molecules, wherein each 5'-RNAY4 specific probe comprises a nucleotide sequence that is the complement to a nucleotide sequence of the 5' end of RNAY4;
forming a complex between one or more 5'-RNAY4 fragments and a 5'-RNAY4 specific oligonucleotide probe; and
removing the 5'-RNAY4:oligonucleotide complexes from the sample.

Each 5'-RNAY4 specific oligonucleotide probe may comprise one or multiple copies of a nucleotide sequence that is the complement to the nucleotide sequence of the 5' end of the RNAY4.

In another embodiment of the method, the step of depleting miR-486-5p fragments from the population of RNA molecules comprises:
adding miR-486-5p specific oligonucleotide probes to a sample containing the population of RNA molecules, wherein each miR-486-5p specific probe comprises a nucleotide sequence that is the complement to a nucleotide sequence of miR-486-5p;
forming a complex between one or more miR-486-5p fragments and a miR-486-5p specific oligonucleotide probe; and
removing the miR-486-5p:oligonucleotide complexes from the sample.

Each miR-486-5p specific oligonucleotide probe may comprise one or multiple copies of a nucleotide sequence that is the complement to the nucleotide sequence of miR-486-5p.

In another embodiment, the 5'end, the 3'end or both ends of each 5'-RNAY4 specific oligonucleotide probe or each miR-486-5p specific oligonucleotide probe are modified, wherein the modification(s) facilitate the removal of the 5'-RNAY4:oligonucleotide complexes and/or miR-486-5p:oligonucleotide complexes from the sample. In a further embodiment, each of the 5'-RNAY4 specific oligonucleotide probes and/or the miR-486-5p specific oligonucleotide probes has a 5' biotin modification, a 3' biotin modification, a 5' dioxigenin modification, a 3' dioxigenin modification, and/or a 5' dinitrophenol modification.

In another embodiment, the 5'-RNAY4 specific oligonucleotide probes and/or the miR-486-5p specific oligonucleotide probes are immobilized on a solid support.

In another aspect, disclosed is a method of improving global gene expression analysis for a population of RNA molecules derived from human blood, plasma and/or serum, the method comprising the step of blocking 5'RNAY4 fragments and/or miR-486-5p in the population of RNA molecules. The method may comprise blocking only 5'-RNAY4 fragments in the population of RNA molecules. The method may comprise blocking only miR-486-5p fragments in the population of RNA molecules. The method may comprise blocking 5'-RNAY4 and miR-486-5p fragments in the population of RNA molecules.

In an embodiment of the method, the step of blocking the 5'RNAY4 fragments in the population of RNA molecules comprises:
  adding 5'-RNAY4 specific oligonucleotide probes to a sample containing the population of RNA molecules, wherein each 5'-RNAY4 specific oligonucleotide probe comprises a nucleotide sequence that is the complement to a nucleotide sequence of the 5' end of the RNAY4; and
  forming a complex between one or more 5'-RNAY4 fragments and a 5'-RNAY4 specific oligonucleotide probe.

In another embodiment, the step of blocking the miR-486-5p fragments in the population of RNA molecules comprises:
  adding miR-486-5p specific oligonucleotide probes to a sample containing the population of RNA molecules, wherein each miR-486-5p specific oligonucleotide probe comprises a nucleotide sequence that is the complement to a nucleotide sequence of miR-486-5p; and
  forming a complex between one or more miR-486-5p fragments and a miR-486-5p specific oligonucleotide probe.

In another embodiment, the 5'end, the 3'end or both ends of each 5'-RNAY4 specific oligonucleotide probe and/or miR-486-5p specific oligonucleotide probe is modified to prevent ligation.

In a further embodiment, the 5'end or the 3'end of each 5'-RNAY4 specific oligonucleotide probe and/or miR-486-5p specific oligonucleotide probe is modified by incorporating a dideoxy nucleotide.

In a further embodiment, the 5'end or the 3'end of each 5'-RNAY4 specific oligonucleotide probe and/or miR-486-5p specific oligonucleotide probe is modified with biotin.

In a further embodiment, the 5'end of each 5'-RNAY4 specific oligonucleotide probe and/or miR-486-5p specific oligonucleotide probe is modified with biotin and the 3'end of each 5'-RNAY4 specific oligonucleotide probe and/or miR-486-5p specific oligonucleotide probe is modified by incorporating a dideoxy nucleotide.

In another embodiment of any of the methods described above, the global gene expression analysis can be microarray analysis, library construction, reverse transcription, amplification, transcriptome profiling, expression analysis and/or sequencing. In a further embodiment, the sequencing is next generation sequencing.

In another aspect, disclosed is a method of performing next generation sequencing of a population of small RNA derived from human blood, plasma and/or serum, the method comprising:
  adding 5'-RNAY4 specific oligonucleotide probes and/or miR-486-5p specific oligonucleotide probes to a sample containing the population of RNA molecules, wherein each 5'-RNAY4 specific oligonucleotide probe comprises a nucleotide sequence that is the complement to a nucleotide sequence of the 5' end of RNAY4 and wherein each miR-486-5p specific oligonucleotide probe comprises a nucleotide sequence that is the complement to a nucleotide sequence of miR-486-5p;
  forming a complex between one or more 5'-RNAY4 fragments and a 5'-RNAY4 specific oligonucleotide probe and/or forming a complex between one or more miR-486-5p fragments and a miR-486-5p specific oligonucleotide probe; and
  removing the 5'-RNAY4:oligonucleotide complexes and/or miR-486-5p:oligonucleotide complexes from the sample, wherein the remaining sample contains a 5'-RNAY4 and/or miR-486-5p depleted population of small RNA molecules;
  preparing a library using the remaining sample; and
  sequencing the library.

In one embodiment, only 5'-RNAY4 specific oligonucleotide probes are added and the remaining sample contains a 5'-RNAY4 depleted population of small RNA molecules. In another embodiment, only miR-486-5p specific oligonucleotide probes are added and the remaining sample contains a miR-486-5p depleted population of small RNA molecules. In a further embodiment, 5'-RNAY4 specific oligonucleotide probes and miR-486-5p specific oligonucleotide probes are added and the remaining sample contains a 5'-RNAY4 and miR-486-5p depleted population of small RNA molecules.

In another embodiment, each 5'-RNAY4 specific oligonucleotide probe comprises one or multiple copies of a nucleotide sequence that is the complement to the nucleotide sequence of the 5' end of the RNAY4.

In another embodiment, each miR-486-5p specific oligonucleotide probe comprises one or multiple copies of a nucleotide sequence that is the complement to the nucleotide sequence of miR-486-5p.

In another embodiment, the 5'-RNAY4:oligonucleotide complexes and/or miR-486-5p:oligonucleotide complexes are removed by size exclusion chromatography.

In another embodiment, the 5'-RNAY4:oligonucleotide complexes and/or miR-486-5p:oligonucleotide complexes are removed by using silicon carbide.

In a further embodiment, the step of removing the 5'-RNAY4:oligonucleotide complexes and/or miR-486-5p: oligonucleotide complexes from the sample comprises:
  combining the sample with a binding buffer, an alcohol and a silicon carbide slurry to provide a binding mixture, wherein the alcohol concentration of the binding mixture is about 1-30% (v/v) to affect selective binding of the 5'-RNAY4:oligonucleotide complexes and/or miR-486-5p:oligonucleotide complexes to the silicon carbide;
  removing the 5'-RNAY4:oligonucleotide complexes and/or miR-486-5p:oligonucleotide complexes bound SiC from the sample; and
  collecting the remaining sample containing the 5'-RNAY4 and/or miR-486-5p depleted population of small RNA molecules.

In further embodiment, the step of removing the 5'-RNAY4:oligonucleotide and/or miR-486-5p complexes comprises:
  combining the sample with a binding buffer and alcohol to provide a binding mixture;
  applying the binding mixture to a silicon carbide column, wherein the alcohol concentration of the binding mixture is about 1-30% (v/v) to affect selective binding of the 5'-RNAY4:oligonucleotide complexes and/or miR-486-5p to the silicon carbide;

collecting the column flowthrough containing the 5'-RNAY4 and/or miR-486-5p depleted population of small RNA molecules.

The alcohol concentration of the binding mixture can be about 1-10% (v/v). In a further embodiment, the alcohol is ethanol.

In another embodiment, the 5'end, the 3'end or both ends of each 5'-RNAY4 specific oligonucleotide probe and/or miR-486-5p specific oligonucleotide probe is modified and wherein the 5'-RNAY4:oligonucleotide complexes and/or miR-486-5p:oligonucleotide complexes are removed by:
  selectively binding the 5'-RNAY4:oligonucleotide complexes and/or miR-486-5p:oligonucleotide complexes to a solid support comprising a protein or antibody that specifically interacts with an end modification on the 5'-RNAY4 specific oligonucleotide probe and/or miR-486-5p specific oligonucleotide probe; and
  collecting an unbound fraction of the sample containing the 5'-RNAY4 and/or miR-486-5p depleted population of small RNA molecules.

In a further embodiment, the 5'end or the 3'end of each 5'-RNAY4 specific oligonucleotide probe and/or miR-486-5p specific oligonucleotide probe is modified with biotin and the solid support comprises avidin or streptavidin.

In a further embodiment, the 5'end or the 3'end of each 5'-RNAY4 specific oligonucleotide probe and/or miR-486-5p specific oligonucleotide probe is modified with digoxigenin and the solid support comprises digoxigenin specific antibodies.

In a further embodiment, the 5'end of each 5'-RNAY4 specific oligonucleotide probe and/or miR-486-5p specific oligonucleotide probe is modified with dinitrophenol and the solid support comprises dinitrophenol specific antibodies.

In a further embodiment, the solid support comprises polymeric beads, which may be magnetic or non-magnetic.

In another aspect, disclosed is a method of performing next generation sequencing of a population of small RNA derived from human blood, plasma and/or serum, the method comprising:
  adding 5'-RNAY4 specific oligonucleotide probes and/or miR-486-5p specific oligonucleotide probes to a sample containing the population of RNA molecules, wherein each 5'-RNAY4 specific oligonucleotide probe comprises a nucleotide sequence that is the complement to a nucleotide sequence of the 5' end of RNAY4 and wherein each miR-486-5p specific oligonucleotide probe comprises a nucleotide sequence that is the complement to a nucleotide sequence of miR-486-5p;
  forming a complex between one or more 5'-RNAY4 fragments and a 5'-RNAY4 specific oligonucleotide probe and/or forming a complex between one or more miR-486-5p fragments and a miR-486-5p specific oligonucleotide probe to provide a 5'-RNAY4 and/or miR-486-5p blocked sample;
  preparing a library using the 5'-RNAY4 and/or miR-486-5p blocked sample; and
  sequencing the library.

In one embodiment, the 5'end, the 3'end or both ends of each 5'-RNAY4 specific oligonucleotide probe and/or miR-486-5p specific oligonucleotide probe is modified to prevent ligation.

In a further embodiment, the 5'end or the 3'end of each 5'-RNAY4 specific oligonucleotide probe and/or miR-486-5p specific oligonucleotide probe is modified by incorporating a dideoxy nucleotide.

In a further embodiment, the 5'end or the 3'end of each 5'-RNAY4 specific oligonucleotide probe and/or miR-486-5p specific oligonucleotide probe is modified with biotin.

In a further embodiment, the 5'end of each 5'-RNAY4 specific oligonucleotide probe and/or miR-486-5p specific oligonucleotide probe is modified with biotin and the 3'end of each 5'-RNAY4 specific oligonucleotide probe and/or miR-486-5p specific oligonucleotide probe is modified by incorporating a dideoxy nucleotide.

In a further aspect, disclosed are kits that are useful for improving global gene expression analysis for a population of RNA molecules derived from human blood, plasma and/or serum. The kit comprises one or more 5'-RNAY4 specific oligonucleotide probes, wherein each 5'-RNAY4 specific oligonucleotide probe comprises a nucleotide sequence that is the complement to a nucleotide sequence of the 5' end of the RNAY4 and optionally, one or more miR-486-5p specific oligonucleotide probes, wherein each miR-486-5p specific oligonucleotide probe comprises a nucleotide sequence that is the complement to a nucleotide sequence of miR-486-5p.

In one embodiment, the 5'end, the 3'end or both ends of each 5'-RNAY4 specific oligonucleotide probe and/or miR-486-5p specific oligonucleotide probe is modified.

In a further embodiment, the 5'end or the 3'end of each 5'-RNAY4 specific oligonucleotide probe and/or miR-486-5p specific oligonucleotide probe is modified with biotin.

In a further embodiment, the 5'end or the 3'end of each 5'-RNAY4 specific oligonucleotide probe and/or miR-486-5p specific oligonucleotide probe is modified with digoxigenin.

In a further embodiment, the 5'end of each 5'-RNAY4 specific oligonucleotide probe and/or miR-486-5p specific oligonucleotide probe is modified with dinitrophenol.

In a further embodiment, the 3'end of each 5'-RNAY4 specific oligonucleotide probe and/or miR-486-5p specific oligonucleotide probe is modified by incorporating a dideoxy nucleotide.

In a further embodiment, the 5'end of each 5'-RNAY4 specific oligonucleotide probe and/or miR-486-5p specific oligonucleotide probe is modified with biotin and the 3'end of each 5'-RNAY4 specific oligonucleotide probe and/or miR-486-5p specific oligonucleotide probe is modified by incorporating a dideoxy nucleotide.

In a further embodiment, wherein the 5'-RNAY4 specific oligonucleotide probe and/or miR-486-5p specific oligonucleotide probe is immobilized on a solid support.

In an embodiment of any of the methods or kits described above, the nucleotide sequence of the 5' end of the RNAY4 has at least 90% sequence identity to the nucleotide sequence of SEQ ID NO: 1. In a further embodiment, the nucleotide sequence of the 5' end of the RNAY4 comprises the nucleotide sequence of SEQ ID NO: 1.

In another embodiment of any of the methods or kits described above, the nucleotide sequence of miR-486-5p has at least 90% sequence identity to the nucleotide sequence of SEQ ID NO: 3. In a further embodiment, the nucleotide sequence of miR-486-5p comprises the nucleotide sequence of SEQ ID NO: 3.

In another embodiment of any of the methods or kits described above, the 5'-RNAY4 specific oligonucleotide probe has at least 90% sequence identity to the nucleotide sequence of SEQ ID NO: 2. In a further embodiment, the 5'-RNAY4 specific oligonucleotide probe comprises the nucleotide sequence of SEQ ID NO: 2.

In another embodiment of any of the methods or kits described above, the miR-486-5p specific oligonucleotide probe has at least 90% sequence identity to the nucleotide sequence of SEQ ID NO: 4. In a further embodiment, the miR-486-5p specific oligonucleotide probe comprises the nucleotide sequence of SEQ ID NO: 4.

DESCRIPTION

Figure 1:
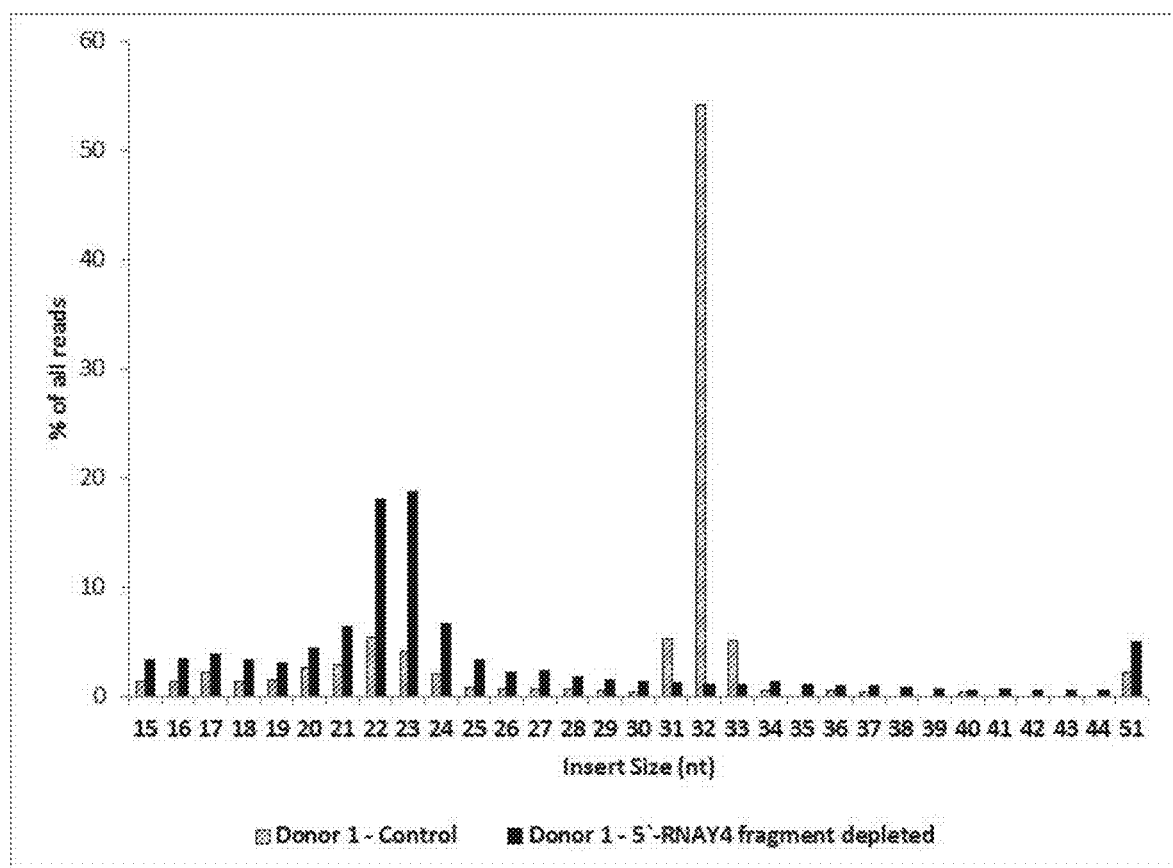
FIG. 1 is a graph of insert sizes corresponding to the overall % of reads for a control (non-depleted) plasma RNA sample and a 5'-RNAY4 fragment-depleted plasma RNA sample from a healthy donor (Donor 1).

It has now been demonstrated that the disproportionate abundance of 5'-RNAY4 fragments in human blood, plasma and serum RNA samples poses a major impediment to accurate detection and quantification of other, better characterized and/or more diagnostically relevant RNAs, such as miRNA. The challenges experienced in the generation of a global expression profile of miRNA in circulation—due to the sheer amount of the 5' end of-RNAY4 present in human blood, plasma and serum—are well exemplified in global gene expression analysis employing next generation sequencing (NGS).

There are many different platforms that can be used for NGS of small RNA, including Roche 454, Roche GS FLX Titanium, Illumina MiSeq, Illumina HiSeq, Illumina Genome Analyzer IIX, Illumina MiniSeq, Illumina NextSeq, Illumina NovaSeq Life Technologies SOLiD4, Life Technologies Ion Proton, Complete Genomics, Helicos Biosciences Heliscope, and Pacific Biosciences SMRT. All of these different platforms follow the same general procedure for NGS of small RNA. Namely, a DNA sequencing library is prepared using purified RNA. Library preparation includes transcribing the RNA into cDNA, ligating the cDNA molecules with 5' and 3' adaptors, and amplifying the ligated DNA fragments. These relatively short DNA fragments are then massively parallel sequenced and bioinformatics analysis applied to de-multiplex samples, align, annotate and aggregate reads.

The number of times each sequence in the library has been "read" (e.g. sequenced) is of utmost importance in determining both how reliably it can be called and its abundance relative to other sequences in the same sample. As the 5' end of RNAY4 is one of the most abundant sequence in human blood, plasma and serum, the greatest proportion (~50-70%) of the reads in any given small RNA library—prepared from RNA purified from blood, plasma and serum—is mapped to RNAY4 (Dhahbi et al., 2013; Brenu et al., 2014). As the total number of all reads for any sample on any NGS platform is finite, a much smaller proportion of reads is allocated for other sequences (~10% for miRNA), which may be of a much greater interest than RNAY4 (Dhahbi et al., 2013; Brenu et al., 2014). In the case of global miRNA expression analysis, this produces much less reliable data, especially for relatively rare miRNA transcripts, which may be read at the level of "noise", or not called at all, because they constitute a very small proportion of the sequencing library at the outset.

Without being limited to a specific theory, it is believed that due to its similar structure and size to miRNA, the 5'-RNAY4 fragments will compete with miRNA during the preparation of a sequencing library at each preparation step (e.g. cDNA transcription, adaptor ligation, amplification) resulting in the creation of a sequencing library that predominantly contains 5'-RNAY4 fragments. As a result, the highly abundant 5'-RNAY4 fragments found in human blood, plasma and serum derived RNA is wasting sequencing capacity and using up the available resources present in the sequencing reaction during NGS.

It has now been surprisingly found that global gene expression analysis for small RNA samples derived from human blood, plasma and serum samples can be improved by selectively depleting the abundant 5'-RNAY4 fragments prior to library preparation or by selectively blocking the 5'-RNAY4 fragments in the RNA samples to prevent them from acting as a substrate during library preparation. By selectively depleting or blocking the 5'-RNAY4 fragments, it is possible to improve the ratio of useful data (e.g. data mapped to miRNAs) to non-useful data (e.g. data mapped to 5'-RNAY4 fragments). As a result, global gene expression analysis can be improved, for example, by increasing the sensitivity of the global gene expression analysis (e.g. reduction of background noise) and by increasing the reliability of the obtained expression data.

Within the total population of miRNAs present in human blood, plasma and serum, it also has been found that certain miRNAs are disproportionately abundant. One of the most overrepresented miRNA is miR-486-5p, which can account for over 50% of the miRNA present in in human blood, plasma and/or serum. miR-486-5p has been extensively studied in many biological pathways including the ubiquitin proteasome pathway (NF-kappa B pathway), and has been generally observed to be reduced in human cancer (Song et al., 2015). It has now been demonstrated that the disproportionate abundance of miR-486-5p in human blood, plasma, and serum RNA samples poses a major impediment to accurate detection and quantification of other, less abundant and/or potentially predictive miRNAs. The challenges experienced in the generation of a global expression profile of miRNA in circulation—due to the sheer amount of miR- 486-5p present in the miRNA found in human blood, plasma and serum—are well exemplified in global gene expression analysis employing NGS.

As noted above, the number of times each sequence in the library has been "read" (e.g. sequenced) is of utmost importance in determining both how reliably it can be called and its abundance relative to other sequences in the same sample and other samples. As miR-486-5p is one of the most abundant miRNA sequence in human blood, plasma and serum, the greatest proportion (~50%) of the miRNA reads from any given small RNA library—prepared from RNA purified from blood, plasma, or serum—is mapped to miR-486-5p (Tonge and Grant, 2016). Further as noted above, the total number of all reads for any sample on any NGS platform is finite. As such, a much smaller proportion of reads is allocated for all the other miRNAs present, which may be of a much greater interest than miR-486-5p. In the case of global miRNA expression analysis, this produces much less reliable data, especially for relatively rare miRNA transcripts, which may be incorporated less efficiently than the most abundant sequences in the library preparation step and therefore read at the level of "noise", or not called at all, because they constitute a very small proportion of the sequencing library at the outset. The sequencing of the library will be skewed towards the sequencing of this overly abundant miR-486-5p.

It has been further surprisingly found that global gene expression analysis for small RNA samples derived from human blood, plasma and serum samples can also be improved by selectively depleting the abundant miR-486-5p fragments prior to library preparation or by selectively blocking the miR-486-5p fragments in the RNA samples to prevent them from acting as a substrate during library preparation. By selectively depleting or blocking the miR-486-5p fragments—and optionally, also selectively depleting or blocking 5'-RNAY4 fragments—it is possible to improve the ratio of useful data (e.g. data mapped to less abundant miRNAs of interest) to non-useful data (e.g. data mapped to miR-486-5p fragments). As a result, global gene expression analysis can be improved, for example, by increasing the sensitivity of the global gene expression analysis (e.g. reduction of background noise) and by increasing the reliability of the obtained expression data. This can be beneficial when performing research and discovery of novel miRNA markers in blood, plasma or serum, as well as studies that rely on the ability to see changes in low expressing but significant miRNA.

Method of Improving Global Gene Expression Analysis of Human Blood/Plasma/Serum Derived RNA Disclosed is a method of improving global gene expression analysis for a population of RNA molecules derived from human blood and more preferably, human plasma and/or serum.

As used herein, "global gene expression analysis" includes any quantitative method for investigating a population of RNA species. In the disclosed method, the population of RNA species are derived from human blood, and more preferably, human plasma and/or serum. Global gene expression analysis can be carried out, for example, by way of microarray analysis, library construction, reverse transcription, amplification, transcriptome profiling, expression analysis and sequencing, including next generation sequencing.

Improving global gene expression analysis in a population of RNA molecules derived from human blood, plasma and/or serum can be achieved by selectively depleting or blocking the 5'-RNAY4 fragments present in the population of RNA molecules, thereby improving the ratio of useful data (e.g. data mapped to miRNAs) to non-useful data (e.g. data mapped to 5'-RNAY4 fragments) obtained by the global gene expression analysis.

Selectively depleting or blocking miR-486-5p fragments present in the population of RNA molecules can also improve global gene expression analysis in a population of RNA molecules derived from human blood, plasma and/or serum. By selectively depleting or blocking the miR-486-5p fragments present in the population of RNA molecules, the ratio of useful data (e.g. data mapped to miRNAs of interest) to non-useful data (e.g. data mapped to miR-486-5p fragments) obtained by the global gene expression analysis is improved.

In one embodiment of the disclosed method of improving global gene expression analysis for a population of RNA molecules derived from human blood, plasma and/or serum comprises selectively depleting or blocking 5'-RNAY4 fragments present in the population of RNA molecules. In another embodiment, the method comprises selectively depleting or blocking miR-486-5p fragments present in the population of RNA molecules. In a further embodiment, the method comprises selectively depleting or blocking 5'-RNAY4 fragments and miR-486-5p fragments present in the population of RNA molecules.

Human Blood, Plasma or Serum Derived RNA Molecules

The disclosed method for improving global gene expression can be performed using an initial population of RNA molecules, which is total RNA isolated from human blood, human plasma or human serum. Whole blood samples can be collected and stored using conventional methods known in the art. It may be desirable to employ blood collection tubes that prevent RNA degradation, such as, but not limited to Paxgene® Blood RNA Tubes (BD Biosciences, Mississauga, Canada), Tempus™ Blood RNA Tubes (Applied Biosystems, Foster City, United States) or Cell-Free RNA BCT® Tubes (Streck, Omaha, United States). Following collection, the whole blood may be separated into plasma or serum fractions using conventional methods known in the art. Methods for the isolation of total RNA from human blood, plasma and/or serum are also well known in the art. Suitable methods for the isolation of total RNA include but are not limited to the use of phenol/chloroform, the use of silicon carbide (SiC), the use of silica, and alcohol precipitation.

The initial population of RNA molecules can also be small RNA isolated from human blood, plasma or serum. Again, suitable methods for the isolation of small RNA are known in the art. Suitable methods include, but are not limited, to the use of phenol/chloroform, the use of silicon carbide, and the use of silica. In a preferred embodiment, the initial population of RNA molecules is small RNA isolated from human blood, plasma and/or serum samples using SiC.

Selective Depletion of 5'-RNAY4 and miR-486-5p Fragments

In one embodiment, disclosed is a method of improving global gene expression analysis for a population of RNA molecules derived from human blood, plasma and/or serum, wherein the method comprises the step of depleting 5'-RNAY4 fragments from the population of RNA molecules. It will be appreciated that the disclosed method does not require the complete removal of all 5'-RNAY4 fragments.

The resulting population of RNA molecules that are depleted of 5'-RNAY4 fragments can be used in downstream global gene expression analysis applications. This method is particularly suitable for preparing small RNA for next generation sequencing applications. By removing the highly abundant 5'-RNAY4 fragments prior to preparation of the sequencing library, the signal to noise ratio can be improved.

5'-RNAY4 fragments can be depleted from the population of RNA molecules by selectively removing the fragments. In one embodiment, 5'-RNAY4 fragments are selectively removed by:
adding 5'-RNAY4 specific oligonucleotide probes to a sample containing the population of RNA molecules, wherein each 5'-RNAY4 specific oligonucleotide probe comprises a nucleotide sequence that is the complement to a nucleotide sequence of the 5' end of RNAY4;
forming a complex between one or more 5'-RNAY4 fragments and a 5'-RNAY4 specific oligonucleotide probe; and
removing the 5'-RNAY4:oligonucleotide complexes from the sample.

The 5'-RNAY4 specific oligonucleotide probes are designed to be complementary to the 5' end of RNAY4, and thus are capable of hybridizing with the 5'-RNAY4 fragments. The 5'-RNAY4 specific oligonucleotide probe can be various lengths, so long as it contains sufficient bases to allow the probe to specifically bind to the 5'-RNAY4 fragments. The 5'-RNAY4 specific oligonucleotide probe may be 6-200 bases and more preferably 20-50 bases.

In a more preferred embodiment, the 5'-RNAY4 specific oligonucleotide probe is designed to be the complement of the 32 base 5'-RNAY4 fragment with the sequence:

(SEQ ID NO: 1)
5'-GGCUGGUCCGAUGGUAGUGGGUUAUCAGAACU-3'.

In this embodiment, the 5'-RNAY4 specific oligonucleotide probe can comprise the following sequence:

(SEQ ID NO: 2)
5'-AGTTCTGATAACCCACTACCATCGGACCAGCC-3'.

In further preferred embodiments, the 5'-RNAY4 specific oligonucleotide probe can be designed to be the complement of a nucleotide having at least 90%, 95% or 99% identity with the nucleotide sequence of SEQ ID NO:1. The 5'-RNAY4 specific oligonucleotide probe can comprise a nucleotide sequence having at least 90%, 95% or 99% identity with the nucleotide sequence of SEQ ID NO:2.

In a further embodiment, the 5'-RNAY4 specific oligonucleotide probe may comprise one or multiple copies of the complement to the 5'-RNAY4 fragment. The 5'-RNAY4 specific oligonucleotide probe may comprise 2-20 copies of the complement to the 5'-RNAY4 fragment, and more preferably comprises 7 copies of the complement to the 5'-RNAY4 fragment.

After hybridization, the 5'-RNAY4:oligonucleotide complexes are removed from the RNA sample to provide the 5'-RNAY4 depleted population of RNA molecules. A variety of different methods can be employed to remove the 5'-RNAY4:oligonucleotide complexes from the RNA sample.

In one embodiment, the 5'-RNAY4 specific oligonucleotide probe includes modifications to facilitate the use of solid supports for the selective removal of the 5'-RNAY4:oligonucleotide complexes. For example, the 5'-RNAY4 specific oligonucleotide probe may include a 5'end modification, a 3'end modification, an internal modification or combination thereof, that allows the 5'-RNAY4:oligonucleotide complexes to covalently or non-covalently bind to a solid support, which comprises a functional group, a protein or an antibody, which specifically interacts with the modification. For example, the oligonucleotide probe can be provided with a 5' or 3' biotin modification for selective binding to solid supports comprising avidin or streptavidin. The oligonucleotide probe can be provided with a 5' or 3' digoxigenin modification for selective binding to solid supports comprising digoxigenin specific antibodies. The oligonucleotide probe can be provided with a 5' dinitrophenol modification for selective binding to solid supports comprising dinitrophenol specific antibodies. Examples of solid supports that may be used to selectively remove 5'-RNAY4:oligonucleotide complexes include resin packed columns and purification beads, which may be magnetic or non-magnetic (such as polystyrene).

In a preferred embodiment, the 5'-RNAY4:oligonucleotide complexes are removed by:
selectively binding to the 5'-RNAY4:oligonucleotide complexes a solid support comprising a protein or antibody that specifically interacts with an end modification on the oligonucleotide probe; and
collecting an unbound fraction of the sample containing the 5'-RNAY4 depleted population of small RNA molecules.

The 5'-RNAY4 specific oligonucleotide probe preferably comprises a 5'end or a 3'end biotin modification and the solid support preferably comprises magnetic beads that are coupled to avidin or streptavidin. In a further preferred embodiment, the magnetic beads are coupled to streptavidin. Following selectively binding of the 5'-RNAY4:oligonucleotide complexes to the magnetic beads, the bound magnetic beads can be removed from the RNA sample using a magnet, thereby removing the 5'RNAY4:oligonucleotide complex from the RNA sample. The unbound fraction of RNA sample containing the 5'-RNAY4 depleted population of small RNA molecules can then be collected for use in downstream global gene expression analysis applications.

In another embodiment, the 5'-RNAY4 specific oligonucleotide probes can be immobilized onto a solid support. In this embodiment, that RNA sample containing the population of RNA molecules can be added to the solid support or vice versa. 5'-RNAY4 fragments will hybridize to the oligonucleotide probes immobilized on the solid support. The unbound fraction of the sample containing the 5'-RNAY4 depleted population of small RNA molecules can then be collected for use in downstream global gene expression analysis applications.

In another embodiment, the 5'-RNAY4:oligonucleotide complexes can be removed from the RNA sample using size exclusion chromatography, which is based on the differential binding of molecules to a matrix based on size. In a preferred embodiment, silica columns can be used to separate the 5'-RNAY4:oligonucleotide complexes from the mixture.

In a further embodiment, the 5'-RNAY4:oligonucleotide complexes can be removed from the RNA sample using a size selective isolation method employing SiC. The RNA sample containing the 5'-RNAY4:oligonucleotide complexes can be combined with a binding buffer, an alcohol and SiC to provide a binding mixture. The alcohol concentration of the binding mixture is adjusted to determine the cut-off size of RNA molecules that will be preferentially bound to the SiC. By using a lower alcohol concentration, the larger 5'-RNAY4:oligonucleotide complexes contained in the RNA sample will selectively bind to the SiC, whereas the smaller miRNAs will remain in the liquid phase.

The alcohol concentration in the binding mixture can be adjusted using any alcohol known in the art. Examples of suitable alcohols include are but not limited to ethanol, isopropanol and methanol. To achieve size selective binding of the 5'-RNAY4:oligonucleotide complexes to the SiC, the alcohol concentration of the binding mixture can preferably be adjusted with ethanol to a concentration of between 1-30% (v/v), and more preferably between 1-10% (v/v).

The size selective isolation method can be performed using a SiC slurry or a SiC column. In either embodiment, the size selective binding step can be performed under low salt conditions and slightly acidic to neutral pH conditions of about pH 4-7. The larger 5'-RNAY4:oligonucleotide complexes contained in the RNA sample will come into contact with the SiC and selectively bind to the SiC particles. The unbound small miRNAs will remain in the liquid phase. In embodiments employing SiC in a slurry format, the liquid phase containing the small miRNAs can be collected, for example, by pelleting the SiC through centrifugation and decanting the liquid phase containing the small miRNAs. For embodiments using a SiC column, such as a spin column, the larger 5'-RNAY4:oligonucleotide complexes selectively bound to the SiC will be retained in the column and the flowthrough collected. The collected small miRNAs can be used in downstream global gene expression analysis.

In a further embodiment, disclosed is a method of improving global gene expression analysis for a population of RNA molecules derived from human blood, plasma and/or serum, wherein the method comprises the step of depleting miR-486-5p fragments from the population of RNA molecules. It will be appreciated that the disclosed method does not require the complete removal of all miR-486-5p fragments The miR-486-5p fragments can be depleted from the population of RNA molecules by selectively removing the fragments. In one embodiment, miR-486-5p fragments are selectively removed by:

adding miR-486-5p specific oligonucleotide probes to a sample containing the population of RNA molecules, wherein each probe comprises a nucleotide sequence that is the complement to the nucleotide sequence of miR-486-5p;

forming a complex between one or more miR-486-5p fragments and a miR-486-5p specific oligonucleotide probe; and removing the miR-486-5p:oligonucleotide complexes from the sample.

The miR-486-5p specific oligonucleotide probe can be various lengths, so long as it contains sufficient bases to allow the probe to specifically bind to the miR-486-5p fragments. The oligonucleotide probe may be 6-200 bases and more preferably 20-50 bases.

In a more preferred embodiment, the oligonucleotide probe is designed to be the complement of the 22 base miR-486-5p fragment having the sequence:

(SEQ ID NO: 3)
5'-UCCUGUACUGAGCUGCCCCGAG-3'.

In this embodiment, the oligonucleotide probe can comprise the following sequence:

(SEQ ID NO: 4)
5'-CTCGGGGCAGCTCAGTACAGGA-3'.

In further preferred embodiments, the miR-486-5p specific oligonucleotide probe can be designed to be the complement of a nucleotide having at least 90%, 95% or 99% identity with the nucleotide sequence of SEQ ID NO:3.

The miR-486-5p specific oligonucleotide probe can comprise a nucleotide sequence having at least 90%, 95% or 99% identity with the nucleotide sequence of SEQ ID NO:4.

In a further embodiment, the oligonucleotide probe may comprise one or multiple copies of the complement to the miR-486-5p fragment. The miR-486-5p specific oligonucleotide probe may comprise 2-20 copies of the complement to the miR-486-5p fragment, and more preferably comprises 7 copies of the complement to the miR-486-5p fragment.

After hybridization, the miR-486-5p:oligonucleotide complexes are removed from the RNA sample to provide the miR-486-5p depleted population of RNA molecules. A variety of different methods can be employed to remove the miR-486-5p:oligonucleotide complexes from the RNA sample including selective binding to a solid support and size selective isolation using a SiC slurry or a SiC column as described above. It will be apparent to the skilled person that the methods described herein for the removal of 5'-RNAY4:oligonucleotide complexes can be adapted for the removal of miR-486-5p:oligonucleotide complexes, for example, through the use of modified miR-486-5p specific oligonucleotide probes.

The disclosed method of improving global gene expression analysis for a population of RNA molecules derived from human blood, plasma and/or serum may comprise the selective depletion of 5'-RNAY4 fragments or the selective depletion miR-486-5p fragments. In alternate embodiments, the method may comprise the selective depletion of 5'-RNAY4 fragments and miR-486-5p fragments, wherein the step depleting of 5'-RNAY4 fragments and the step of depleting the miR-486-5p fragments are carried out successively or concurrently.

Selective Blocking of 5'-RNAY4 and miR-486-5p Fragments

In another embodiment, disclosed is a method of improving global gene expression analysis for a population of RNA molecules derived from human blood, plasma and/or serum, wherein the method comprises the step of selectively blocking 5'-RNAY4 fragments in the population of RNA molecules.

As used herein, "selectively blocking 5'-RNAY4 fragments" refers to any modification that renders the 5'-RNAY4 fragments an unsuitable substrate in a downstream global gene expression analysis application. For example, the 5'-RNAY4 fragments can be blocked by hybridizing the 5'-RNAY4 fragments with a 5'-RNAY4 specific oligonucleotide probe having a complementary sequence to form 5'-RNAY4:oligonucleotide complexes.

The resulting population of RNA molecules including the blocked 5'-RNAY4 fragments can be used in downstream global gene expression analysis applications. This method is particularly suitable for preparing small RNA for next generation sequencing applications in order to improve the signal to noise ratio. By blocking the highly abundant 5'-RNAY4 fragments (e.g. by forming double stranded DNA-RNA hybrids with the 5'-RNAY4 specific oligonucleotide probes), these fragments will no longer be a suitable substrate for any of the steps in library preparation, including the initial attachment of the 5' and 3' adaptors.

The 5'-RNAY4 fragments can be selectively blocked in a population of RNA molecules by:

adding 5'-RNAY4 specific oligonucleotide probes to a sample containing the population of RNA molecules, wherein each 5'-RNAY4 specific oligonucleotide probe comprises a nucleotide sequence that is the complement to a nucleotide sequence of the 5' end of the RNAY4; and forming a complex between one or more 5'-RNAY4 fragments and a 5'-RNAY4 specific oligonucleotide probe.

Any of the 5'-RNAY4 specific oligonucleotide probes described above can be used to selectively block the 5'-RNAY4 fragments contained in the RNA sample by forming a complex between the 5'-RNAY4 fragments and the 5'-RNAY4 specific oligonucleotide probe.

In a further embodiment, the 5'end, the 3'end or both ends of the 5'-RNAY4 specific oligonucleotide probe is modified to prevent ligation. The 5'end of the 5'-RNAY4 specific oligonucleotide probe can be selectively blocked through the use of inverted dideoxy-T, the use of dephoshorylated 5' ends, the use of biotin and any other suitable 5'end modification method. The 3' end of the 5'-RNAY4 specific oligonucleotide probe can also be blocked using suitable 3'end modification method, including but not limited to, the use of inverted dT, dideoxy-C, and other dideoxy nucleotides.

In a preferred embodiment, the 5'-RNAY4 specific oligonucleotide probe is blocked at both the 5' and 3' end, thereby preventing the attachment of 5' and 3' adaptors to the 5'-RNAY4 specific oligonucleotide probe. By blocking one or both ends of the 5'-RNAY4 specific oligonucleotide probe, it is possible to avoid the 5'-RNAY4 specific oligonucleotide probes themselves being incorporated into the sequence library and contributing to the background noise. In a preferred embodiment, the 5'-RNAY4 specific oligonucleotide probe is blocked using a biotin at the 5' end and using a dideoxy base at the 3' end.

In another embodiment, disclosed is a method of improving global gene expression analysis for a population of RNA molecules derived from human blood, plasma and/or serum, wherein the method comprises the step of selectively blocking miR-486-5p fragments in the population of RNA molecules.

As used herein, "selectively blocking miR-486-5p fragments" refers to any modification that renders the miR-486-5p fragments an unsuitable substrate in a downstream global gene expression analysis application. For example, the miR-486-5p fragments can be blocked by hybridizing the miR-486-5p fragments with a miR-486-5p specific oligonucleotide probe having a complementary sequence to form miR-486-5p:oligonucleotide complexes.

The resulting population of RNA molecules including the blocked miR-486-5p fragments can also be used in downstream global gene expression analysis applications. This method is also particularly suitable for preparing small RNA for next generation sequencing applications in order to improve the signal to noise ratio. By blocking the highly abundant miR-486-5p fragments (e.g. by forming double stranded DNA-RNA hybrids with the miR-486-5p specific oligonucleotide probes), these fragments will no longer be a suitable substrate for any of the steps in library preparation, including the initial attachment of the 5' and 3' adaptors.

The miR-486-5p fragments can be selectively blocked in a population of RNA molecules by:
  adding miR-486-5p specific oligonucleotide probes to a sample containing the population of RNA molecules, wherein each miR-486-5p specific oligonucleotide probe comprises a nucleotide sequence that is the complement to a nucleotide sequence of miR-486-5p; and
  forming a complex between one or more miR-486-5p fragments and a miR-486-5p specific oligonucleotide probe.

Any of the miR-486-5p specific oligonucleotide probes described above can be used to selectively block the miR-486-5p fragments contained in the RNA sample by forming a complex between the miR-486-5p fragments and the miR-486-5p specific oligonucleotide probe.

In a further embodiment, the 5'end, the 3'end or both ends of the miR-486-5p specific oligonucleotide probe are modified to prevent ligation. The miR-486-5p specific oligonucleotide probe can be similarly modified as described above for modified 5'-RNAY4 specific oligonucleotide probes.

The disclosed method may comprise selectively blocking of 5'-RNAY4 fragments or selectively blocking miR-486-5p fragments. In alternate embodiments, the method may comprise selectively blocking of 5'-RNAY4 fragments and miR-486-5p fragments, wherein the step blocking 5'-RNAY4 fragments and the step of blocking miR-486-5p fragments are carried out successively or concurrently.

Next Generation Sequencing and Small RNA Libraries

Further disclosed is a method of performing next generation sequencing of a population of small RNA derived from human blood, plasma and/or serum. In one embodiment, the method comprises the provision of a 5'-RNAY4 fragment depleted population of small RNA molecules, which is then used to prepare the sequencing library. By removing the highly abundant 5'-RNAY4 fragments prior to the preparation of the sequencing library, the sequencing capacity for the less abundant small RNA species is increased and the efficiency of the sequencing reaction improved. Fewer resources are wasted during both the library preparation and sequencing steps since the depleted 5'-RNAY4 fragments will not form part of the sequencing library and will therefore not be read during the sequencing.

In a preferred embodiment, the method of performing next generation sequencing of a population of small RNA derived from human blood, plasma and/or serum comprises:
  adding 5'-RNAY4 specific oligonucleotide probes to a sample containing the population of RNA molecules, wherein each probe comprises a nucleotide sequence that is the complement to a nucleotide sequence of the 5' end of RNAY4;
  forming a complex between one or more 5'-RNAY4 fragments and a 5'-RNAY4 specific oligonucleotide probe; and
  removing the 5'-RNAY4:oligonucleotide complexes from the sample, wherein the remaining sample contains a 5'-RNAY4 depleted population of small RNA molecules;
  preparing a library using the remaining sample; and
  sequencing the library.

The 5'-RNAY4 depletion steps can be performed as described in greater detail above. The library preparation steps and sequencing steps can be performed in accordance with known NGS protocols.

In another embodiment, the method of performing next generation sequencing of a population of small RNA derived from human blood, plasma and/or serum comprises blocking the 5'-RNAY4 fragments contained in the population of RNA molecules to be sequence, prior to the preparation of the library. By blocking the 5'-RNAY4 fragments before the library is generated, the sequencing capacity for the less abundant small RNA species is increased and the efficiency of the sequencing reaction improved. Fewer resources are wasted during both the library preparation and sequencing steps since the blocked 5'-RNAY4 fragments will not act as a substrate during the library preparation and will therefore not be read during the sequencing. Further, by using 5'end and/or 3'end modified 5'-RNAY4 specific oligonucleotide probes which are themselves blocked, incorporation of the oligonucleotide probes into the sequence library and the consequential increase in background noise can be avoided.

In a preferred embodiment, disclosed is a method of performing next generation sequencing of small RNA from a sample, comprising:
adding 5'-RNAY4 specific oligonucleotide probes to a sample containing the population of RNA molecules, wherein each 5'-RNAY4 specific oligonucleotide probe comprises a nucleotide sequence that is the complement to a nucleotide sequence of the 5' end of the RNAY4; and
forming a complex between one or more 5'-RNAY4 fragments and a 5'-RNAY4 specific oligonucleotide probe to provide a 5'-RNAY4 blocked sample;
preparing a library using the 5'-RNAY4 blocked sample; and
sequencing the library.

The 5'-RNAY4 blocking steps can be performed as described in greater detail above. In a further embodiment, the 5'-RNAY4 specific oligonucleotide probe can be modified at the 5'end, the 3' end or at both ends as described above in greater detail.

The library preparation steps and sequencing steps can be performed in accordance with known NGS protocols.

In another embodiment, the method comprises the provision of a miR-486-5p fragment depleted population of small RNA molecules, which is then used to prepare the sequencing library. By removing the highly abundant miR-486-5p fragments prior to the preparation of the sequencing library, the sequencing capacity for the less abundant small RNA species is increased and the efficiency of the sequencing reaction improved. Fewer resources are wasted during both the library preparation and sequencing steps since the depleted miR-486-5p fragments will not form part of the sequencing library and will therefore not be read during the sequencing.

In a preferred embodiment, the method of performing next generation sequencing of a population of small RNA derived from human blood, plasma and/or serum comprises:
adding miR-486-5p specific oligonucleotide probes to a sample containing the population of RNA molecules, wherein each probe comprises a nucleotide sequence that is the complement to a nucleotide sequence of miR-486-5p;
forming a complex between one or more miR-486-5p fragments and a miR-486-5p specific oligonucleotide probe; and
removing the miR-486-5p:oligonucleotide complexes from the sample, wherein the remaining sample contains a miR-486-5p depleted population of small RNA molecules;
preparing a library using the remaining sample; and
sequencing the library.

The miR-486-5p depletion steps can be performed as described in greater detail above. The library preparation steps and sequencing steps can be performed in accordance with known NGS protocols.

In another embodiment, the method of performing next generation sequencing of a population of small RNA derived from human blood, plasma and/or serum comprises blocking the miR-486-5p fragments contained in the population of RNA molecules to be sequence, prior to the preparation of the library. By blocking the miR-486-5p fragments before the library is generated, the sequencing capacity for the less abundant small RNA species is increased and the efficiency of the sequencing reaction improved. Fewer resources are wasted during both the library preparation and sequencing steps since the blocked miR-486-5p fragments will not act as a substrate during the library preparation and will therefore not be read during the sequencing. Further, by using 5'end and/or 3'end modified oligonucleotide probes which are themselves blocked, incorporation of the oligonucleotide probes into the sequence library and the consequential increase in background noise can be avoided.

In another embodiment, disclosed is a method of performing next generation sequencing of small RNA from a sample, comprising:
adding miR-486-5p specific oligonucleotide probes to a sample containing the population of RNA molecules, wherein each miR-486-5p specific oligonucleotide probe comprises a nucleotide sequence that is the complement to a nucleotide sequence of miR-486-5p; and
forming a complex between one or more miR-486-5p fragments and a miR-486-5p specific oligonucleotide probe to provide a miR-486-5p blocked sample;
preparing a library using the miR-486-5p blocked sample; and
sequencing the library.

The miR-486-5p blocking steps can be performed as described in greater detail. In a further embodiment, the miR-486-5p specific oligonucleotide probe can be modified at the 5'end, the 3' end or both ends. The miR-486-5p specific oligonucleotide probe can be similarly modified as described above for modified 5'-RNAY4 specific oligonucleotide probes.

The library preparation steps and sequencing steps can be performed in accordance with known NGS protocols.

In one embodiment, the disclosed method of performing next generation sequencing may comprise the preparation of a library using a 5'-RNAY4 depleted population of small RNA molecules or a miR-486-5p depleted population of small RNA molecules. In an alternate embodiment, the method may comprise the preparation of a library using a 5'-RNAY4 and miR-486-5p depleted population of small RNA molecules, wherein the steps of depleting the 5'-RNAY4 fragments and the miR-486-5p fragments are carried out successively or concurrently.

In another embodiment, the disclosed method of performing next generation sequencing may comprise the preparation of a library using a 5'-RNAY4 blocked sample or a miR-486-5p blocked sample. In an alternate embodiment, the method may comprise the preparation of a library using a 5'-RNAY4 blocked and a miR-486-5p blocked sample, wherein the steps of selectively blocking the 5'-RNAY4 fragments and the miR-486-5p fragments are carried out successively or concurrently.

Kits for Improving Global Gene Expression Analysis

Further disclosed, is a kit for improving global gene expression analysis for a population of RNA molecules derived from human blood, plasma and/or serum. The kit can comprise one or more 5'-RNAY4 specific oligonucleotide probes, wherein each 5'-RNAY4 specific oligonucleotide probe comprises a nucleotide sequence that is the complement to a nucleotide sequence of the 5' end of the RNAY4.

The kit may comprise any of the 5'-RNAY4 specific oligonucleotide probes described in greater detail above. The 5'-RNAY4 specific oligonucleotide probes can be used to block the fragments containing the 5' end of the RNAY4 by forming 5'-RNAY4:oligonucleotide complexes. In a preferred embodiment, such 5'-RNAY4 specific oligonucleotide probes include a 5'end and/or 3'end modification to prevent ligation of the probes. For example, the 5'end or the 3'end can be modified by incorporating a dideoxy nucleotide as described in greater detail above.

Alternatively, the 5'-RNAY4 specific oligonucleotide probes can be used to form 5'-RNAY4:oligonucleotide complexes, which are subsequently removed from the population of RNA molecules. The 5'-RNAY4 specific oligonucleotide probes may include a modification to facilitate removal of the 5'-RNAY4:oligonucleotide complex from a sample using a solid support. For example, the 5'end or the 3'end of the oligonucleotide probe can be modified with biotin for use with avidin or streptavidin coupled solid supports. Further examples of suitable modifications for use with solid supports are described in greater detail above.

The kit may further comprise any of the miR-486-5p specific oligonucleotide probes described in greater detail above. The miR-486-5p specific oligonucleotide probes can be used to block the miR-486-5p fragments by forming 5'-RNAY4:oligonucleotide complexes. In a preferred embodiment, such miR-486-5p specific oligonucleotide probes include a 5'end and/or 3'end modification to prevent ligation of the probes. For example, the 5'end or the 3'end can be modified by incorporating a dideoxy nucleotide as described in greater detail above. The same modifications described above for 5'-RNAY4 specific oligonucleotide probes can also be incorporated into miR-486-5p specific oligonucleotide probes.

The miR-486-5p specific oligonucleotide probes can also be used to form miR-486-5p:oligonucleotide complexes, which are subsequently removed from the population of RNA molecules. The miR-486-5p specific oligonucleotide probes may include a modification to facilitate removal of the miR-486-5p:oligonucleotide complex from a sample using a solid support. For example, the 5'end or the 3'end of the miR-486-5p specific oligonucleotide probe can be modified with biotin for use with avidin or streptavidin coupled solid supports. Further examples of suitable modifications for use with solid supports are described in greater detail above. The same modifications described above for 5'-RNAY4 specific oligonucleotide probes can also be incorporated into miR-486-5p specific oligonucleotide probes.

In another embodiment, the 5'-RNAY4 specific oligonucleotide probes and/or the miR-486-5p specific oligonucleotide probes can be provided immobilized on a solid support, such as purification beads, which may be magnetic or non-magnetic.

Although the invention has been described with reference to illustrative embodiments, it is to be understood that the invention is not limited to these precise embodiments, and that various changes and modification are to be intended to be encompassed in the appended claims.

EXAMPLES

These examples are described for the purposes of illustration and are not intended to limit the scope of the invention.

Example 1—Preparation of Capture Probe for 5'-RNAY4 Fragment

The capture probe for the 5'-RNAY4 fragment was designed by using the "*Homo sapiens* RNA, Ro-associated Y4 (RNY4), Y RNA" (NCBI Reference Sequence: NR 004393.1) as a reference sequence for the full length RNAY4 and creating a complement of the first 32 nucleotides in the sequence. This was based on previous observations and sequencing data of small RNA purified form plasma/serum, which showed that the most over-represented sequence in the small RNA fraction of RNA purified from plasma/serum was the 31-33 nucleotide long 5' fragment of RNAY4.

The capture probe was designed to be the complement of the 32 base 5'-RNAY4 fragment having the sequence (SEQ ID NO: 1)
5'-GGCUGGUCCGAUGGUAGUGGGUUAUCAGAACU-3'

The sequence of the oligonucleotide capture probe is:

(SEQ ID NO: 2)
5'-AGTTCTGATAACCCACTACCATCGGACCAGCC-3'

In order to facilitate the removal of the 5'-RNAY4:capture oligonucleotide complexes, biotin was covalently attached to the 5' end of the capture oligonucleotide.

Example 2—Depletion of the 5'-RNAY4 Fragment from Human Plasma

A 10 mL blood sample was collected into a BD Vacutainer® Venous Blood Collection Tube (18 mg K2 EDTA, Spray-Dried) (BD diagnostics) from a single healthy donor. Plasma was then collected from the blood sample by low-speed centrifugation. Total RNA was then purified from 200 µL of the human plasma using Norgen's Plasma/Serum RNA Isolation Mini Kit (Cat #55000, Norgen, Thorold, Canada) according to the provided protocol.

Next, the 5'-RNAY4 fragment was depleted from the total RNA sample using the probe described in Example 1. Briefly, Streptavidin Magnetic Beads were prepared by aliquoting 125 µL (500 µg) of Streptavidin Magnetic Beads (New England Biolabs, Whitby, Canada) into a clean RNase-free microcentrifuge tube, and 100 µL of buffer [0.5 M NaCl, 20 mM Tris-HCl (pH 7.5), 1 mM EDTA] was added to the beads and they were then vortexed to suspend. A magnet was then applied to the side of tube for approximately 30 seconds, and the supernatant was removed and discarded. Next, 1.0 $A_{260}$ unit of the biotin-(5'-RNAY4 fragment capture probe) was dissolved in in 500 µL of buffer [0.5 M NaCl, 20 mM Tris-HCl (pH 7.5), 1 mM EDTA] to a final concentration 8 pmol/µL. Next, 25 µL of the biotin-(5'-RNAY4 fragment capture probe) solution was added to the prepared magnetic beads and vortexed to suspend beads. This was then incubated at room temperature for 5 minutes with occasional agitation by hand, then a magnet was applied and the supernatant was again removed and discarded. The beads were washed by adding 100 µL of buffer [0.5 M NaCl, 20 mM Tris-HCl (pH 7.5), 1 mM EDTA], vortexing to suspend, and then applying a magnet and discarding the supernatant. The beads were then washed a second time in the same manner.

Next, 25 µL of the total RNA purified from plasma was mixed with 25 µL of buffer [1 M NaCl, 40 mM Tris-HCl (pH 7.5), 2 mM EDTA] and heated at 65° C. for 5 minutes then quickly chilled at 4° C. for 3 minutes. The total RNA sample was then added to the previously prepared magnetic beads. The mixture was vortexed to suspend the particles, then incubated at room temperature for 10 minutes with occasional agitation by hand. A magnet was then applied and the supernatant (containing the depleted RNA) was collected. Next, 100 µL of the buffer was again added to the beads, followed by vortexing to suspend the beads. Again a magnet was applied and the supernatant (containing the depleted RNA) was collected. This process was then repeated, for a total of 3 collections of the depleted RNA. Finally, 100 µL of a cold low salt buffer [0.15 M NaCl, 20 mM Tris-HCl (pH 7.5), 1 mM EDTA] was added to beads, and vortexed to suspend. Again, a magnet was applied and the supernatant was removed and collected. All of the recovered supernatants were then pooled.

The 5'-RNAY4 fragment-depleted RNA can be assayed or further processed (e.g. preparation of a sequencing library) immediately or it can be purified prior to the assay. Multiple purification and concentration methods are possible, including through the use of silicon carbide columns, silica columns, gel electrophoresis or ethanol precipitation.

Example 3—Improved Ratio of Useful Data Obtained During Small RNA Next Generation Sequencing of Human Plasma by Selectively Depleting the Highly Abundant 5'-RNAY4 Fragments Two 10 mL blood samples were collected into BD Vacutainer® Venous Blood Collection Tubes (18 mg K2 EDTA, Spray-Dried) (BD Diagnostics, Mississauga, Canada) from two healthy donors. Plasma was then collected from the blood samples by low-speed centrifugation. Total RNA was then purified from 200 µL of the human plasma samples using Norgen's Plasma/Serum RNA Isolation Mini Kit (Cat #55000, Norgen, Thorold, Canada) according to the provided protocol. Next, the 5'-RNAY4 fragment was depleted from 1 of the total RNA samples from each donor using the probe described in Example 1 and the method outlined in Example 2.

The two different samples of 5'-RNAY4 fragment-depleted RNA from the 2 donors were then concentrated using Norgen's Plasma/Serum RNA Isolation Mini Kit (Cat #55000, Norgen, Thorold, Canada) with a slight modification to the first two steps in the provided protocol: 1) The 5'-RNAY4 fragment-depleted RNA was mixed with an equal volume of Lysis Buffer A; and 2) the resulting mixture was then mixed with an equal volume of 96-100% ethanol (for example, a 350 µL RNA sample depleted of 5'-RNAY4 was first mixed with 350 µL of Lysis Buffer A and then mixed with 700 µL of 96-100% ethanol). Subsequently, the provided protocol was followed as specified in the kit insert of Norgen's Plasma/Serum RNA Isolation Mini Kit (Cat #55000, Norgen, Thorold, Canada), starting with Step 3.

The concentrated 5'-RNAY4 fragment-depleted RNA from each donor was then used for small RNA library preparation for downstream NGS analysis. Briefly, using the NEBNext® Multiplex Small RNA Library Prep Set for Illumina® (New England Biolabs, Whitby, Canada), the RNA was first ligated to the 3' adapter, followed by RT primer hybridization and 3' adapter blocking. Next, the 5' adapter was ligated to the 5' end of the RNA, which was then reverse transcribed into cDNA. This was followed by a limited (15) cycle PCR amplification to enrich the cDNA and also to attach the indexing (barcode) sequences. The indexed libraries were then resolved on a 6% TBE gel and the fragments of interest excised from the gel, crushed and left over-night in 200 µL of water to release DNA. The crushed gel pieces were filtered out and the DNA in the filtrate concentrated using Norgen's RNA Clean-Up and Concentration Micro-Elute Kit (Cat #61000, Norgen, Thorold, Canada) according to the provided protocol. All libraries were quantified and assessed for library size by the Agilent Bioanalyzer using the Agilent High Sensitivity DNA Kit (Agilent Technologies, Santa Clara, United States). As a control, the plasma RNA isolated from each individual that was not depleted of the 5'-RNAY4 fragment was also used for small RNA library preparation.

Next, all 4 of the small RNA libraries were sequenced on the Illumina MiSeq® (I lumina Inc., San Diego, United States) instrument according to the instructions provided by the manufacturer (Preparing Libraries for Sequencing on the MiSeq® and the MiSeq® System User Guide). The resulting NGS sequencing data was then analyzed in a number of different ways to verify that the ratio of useful data obtained was improved in the small RNA libraries prepared from plasma that was depleted of the 5' fragment of RNAY4 compared to the control small RNA libraries prepared from non-depleted plasma.

First, the overall number of raw NGS reads mapping to RNAY4 was determined for the control (non-depleted) and the 5'-RNAY4 fragment-depleted RNA, and the results are shown in Table 1. As it can be seen, the non-depleted control samples result in hundreds of thousands of reads that map to RNAY4 (838,670 and 947,622), while the 5'-RNAY4 fragment-depleted RNA resulted in only approximately 100 reads that map to RNAY4. Therefore, the 5'-RNAY4 fragment has been successfully removed from the samples, and the resources in the NGS run can now be used to map and sequence the less abundant miRNA molecules that are present.

TABLE 1

|  | Control (Non-Depleted) Plasma RNA Samples | | 5'-RNAY4 fragment-depleted Plasma RNA Samples | |
| --- | --- | --- | --- | --- |
|  | Donor 1 | Donor 2 | Donor 1 | Donor 2 |
| Number of Reads Mapping to RNAY4 | 838670 | 947622 | 101 | 127 |

Figure 2:
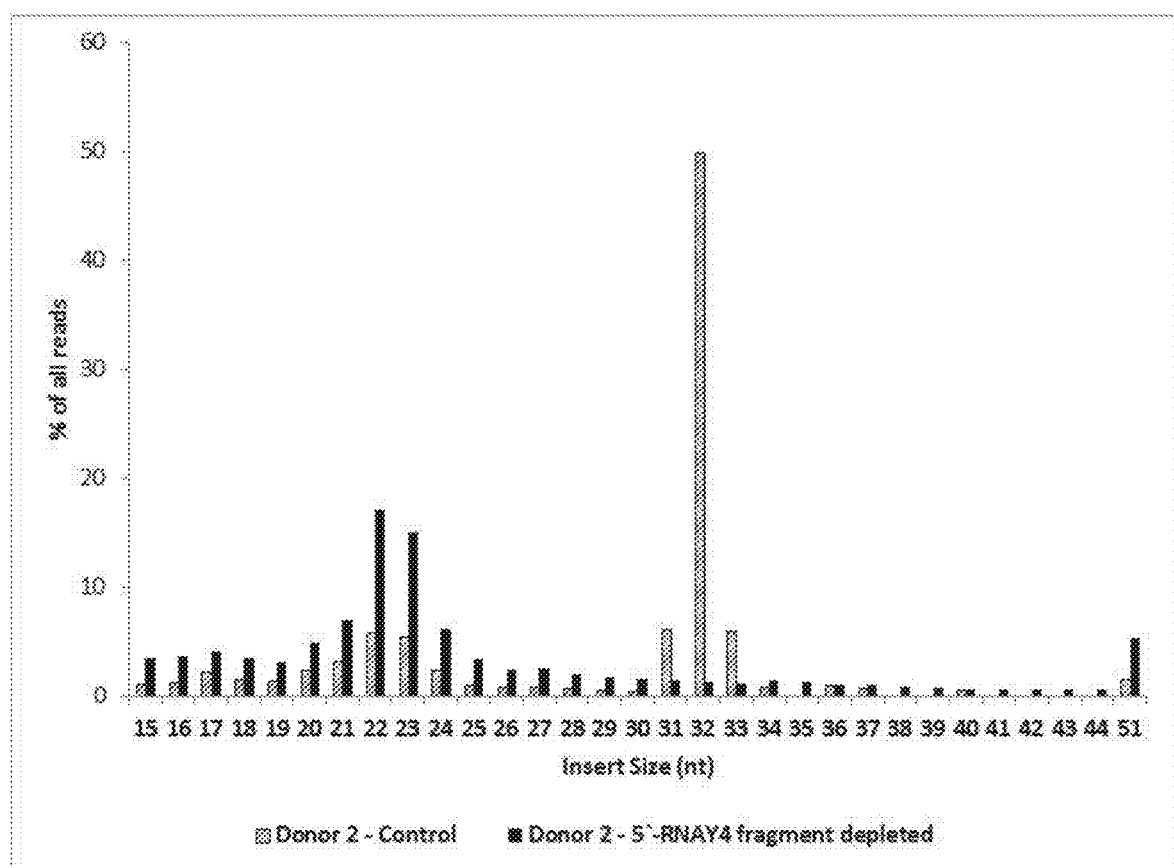
FIG. 2 is a graph of insert sizes corresponding to the overall % of reads for a control (non-depleted) plasma RNA sample and a 5'-RNAY4 fragment-depleted plasma RNA sample from a healthy donor (Donor 2).

Next, the number of reads for each donor was graphed according to insert size incorporated into the library. When performing NGS of small RNA libraries from plasma, the main RNA of interest for analysis is miRNA, which are approximately 20 nt in size. As previously stated, the abundant 5'-RNAY4 fragment is 32 nt in size. Therefore, the depletion of the 5'-RNAY4 fragment can also be verified by determining the % of reads for each insert size. FIG. 1 contains a graph of insert sizes corresponding to the overall % of reads for the control (non-depleted) and the 5'-RNAY4 fragment-depleted RNA for Donor 1, while FIG. 2 contains a graph of insert sizes corresponding to the overall % of reads for the control (non-depleted) and the 5'-RNAY4 fragment-depleted RNA for Donor 2. As can be seen in both figures, the control (non-depleted) library incorporated a majority (50-55%) of 32 nt inserts, and less than 10% of 20-22 nt inserts (striped bars). Therefore, a vast majority of the resources of the NGS run are being used to map and read inserts that are not of interest. In contrast, the 5'-RNAY4 fragment-depleted libraries incorporated a majority (~35-40%) of 22 and 23 nt inserts and showed virtually no 32 nt inserts (black bars). Therefore, by removing the 5'-RNAY4 fragment, valuable resources in the sequencing run will not be wasted on sequencing this one abundant RNA species.

Figure 3:
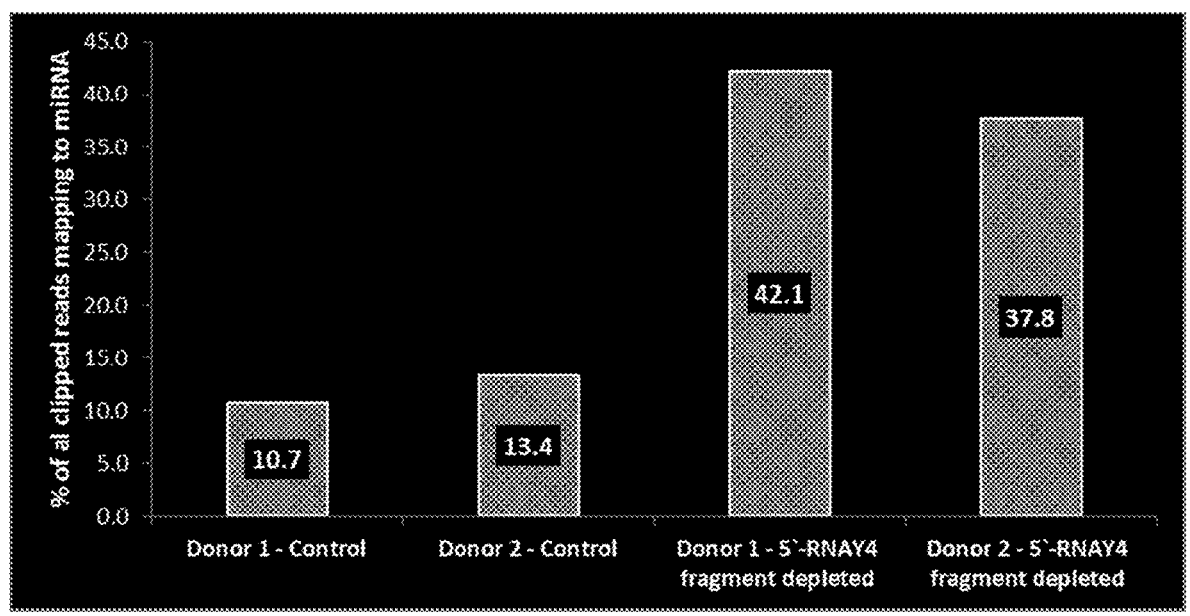
FIG. 3 is a graph depicting the percentage of all reads in next generation sequencing (NGS) runs that map to miRNA from both control (non-depleted) plasma RNA samples from Donor 1 and 2, as well as the 5'-RNAY4 fragment-depleted plasma RNA samples from Donor 1 and 2.

FIG. 3 is a graph depicting the percent of all reads in an NGS run that map to miRNA from both the control (non-depleted) samples from Donor 1 and 2, as well as the 5'-RNAY4 fragment-depleted samples from Donor 1 and 2. For Donor 1, the control sample showed only 10.7% of reads mapping to miRNA inserts, while the 5'-RNAY4 fragment-depleted sample showed 42.1% of reads mapping to miRNA inserts. For Donor 2, the control sample showed only 13.4% of reads mapping to miRNA inserts, while the 5'-RNAY4 fragment-depleted sample showed 37.8% of reads mapping to miRNA inserts. Therefore, 5'-RNAY4 fragment-depletion resulted in significantly more reads that can be mapped to the miRNA inserts of interest, and thus the ratio of useful data obtained during small RNA next generation sequencing of human plasma is greatly improved.

Figure 4:
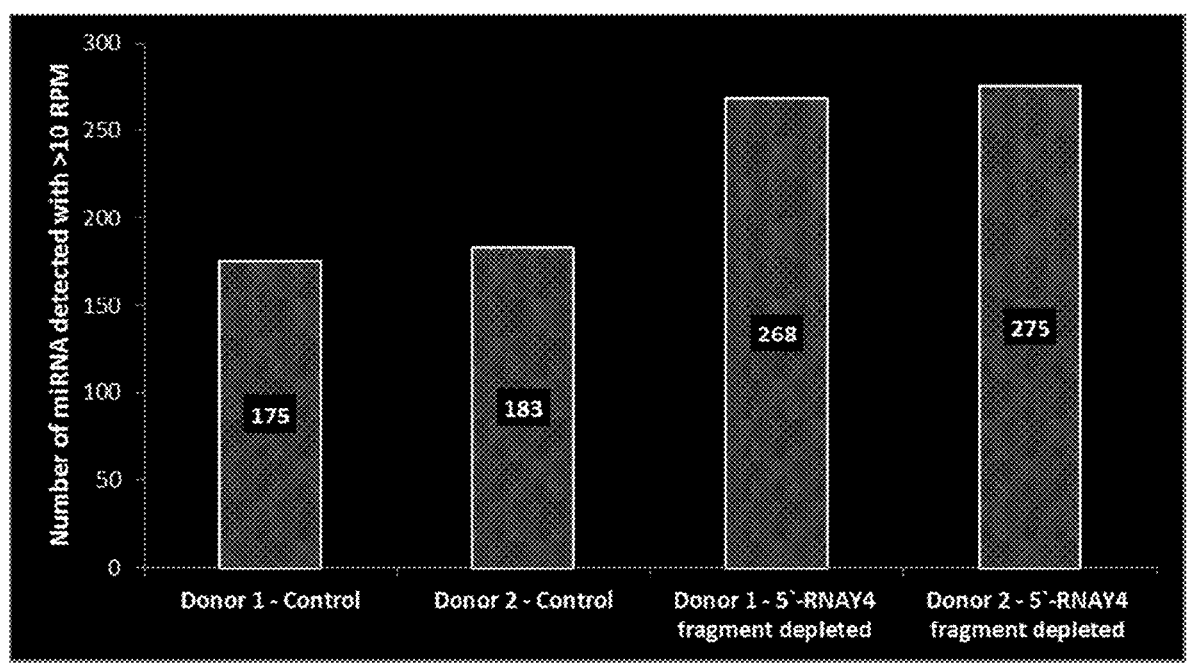
FIG. 4 is a graph depicting the number of miRNA detected in NGS runs from libraries created from both control (non-depleted) plasma RNA samples from Donor 1 and 2, as well as the 5'-RNAY4 fragment-depleted plasma RNA samples from Donor 1 and 2.

FIG. 4 is a graph depicting the number of miRNA detected in NGS runs from libraries created from both the control (non-depleted) samples from Donor 1 and 2, as well as the 5'-RNAY4 fragment-depleted samples from Donor 1 and 2. For Donor 1, the control sample showed 175 miR-NAs, while the 5'-RNAY4 fragment-depleted sample showed 268 miRNA inserts. For Donor 2, the control sample showed 183 miRNAs, while the 5'-RNAY4 fragment-depleted sample showed 275 miRNA inserts. Therefore, 5'-RNAY4 fragment-depletion resulted in a greater sensitivity of miRNA detection in both Donor 1 and Donor 2 because of increased sequencing depth. These results indicate that almost 100 more miRNAs can be reliably called in 5'-RNAY4 fragment-depleted RNA vs. control (non-depleted) RNA, therefore demonstrating that the method of the present invention improves the signal-to-noise ratio and allows for more low-abundance miRNAs to be detected during NGS applications.

Example 4—Preparation of Capture Probe for hsa-miR-486-5p

The capture probe for the miR-486-5p was designed by using the mature sequence hsa-miR-486-5p from miRBase (Accession number MIMAT0002177) as a reference sequence for the full length hsa-miR-486-5p and creating a complement of the nucleotides in the sequence. This was based on previous observations and sequencing data of small RNA purified from blood/plasma/serum, which showed that one of the most over-represented microRNA in the small RNA fraction of RNA purified from blood/plasma/serum was miR-486-5p.

The capture probe was designed to be the complement of the 22 base hsa-miR-486-5p having the sequence:

(SEQ ID NO: 3)
5'-UCCUGUACUGAGCUGCCCCGAG-3'

The sequence of the oligonucleotide capture probe is:

(SEQ ID NO: 4)
5'-CTCGGGGCAGCTCAGTACAGGA-3'

In order to facilitate the removal of the miR-486-5p: capture oligonucleotide complexes, biotin was covalently attached to the 5' end of the capture oligonucleotide.

Example 5—Depletion of the hsa-miR-486-5p Fragment from Human Blood and Plasma

Three mL blood samples were collected into Tempus™ Blood RNA Tubes (Applied Biosystems, Foster City, United States)) from two different healthy donors. Total RNA was then purified from the tubes using Norgen's Preserved Blood RNA Purification Kit I (for use with Tempus™ Blood RNA Tubes) (Cat #43400, Norgen, Thorold, Canada) according to the provided protocol. A 2.5 mL blood sample was collected into a Paxgene® Blood RNA Tube (BD Biosciences, Mississauga, Canada) from a healthy donor. Total RNA was then purified from the tube using Norgen's Preserved Blood RNA Purification Kit II (for use with PAXgene™ Blood RNA Tubes) (Cat #43500, Norgen, Thorold, Canada) according to the provided protocol. A 10 mL blood sample was collected into a BD Vacutainer® Venous Blood Collection Tube (18 mg K2 EDTA, Spray-Dried) (BD diagnostics) from a single healthy donor. Total RNA was then purified from 100 μL of the whole blood using Norgen's Total RNA Purification Kit (Cat #17200, Norgen, Thorold, Canada) according to the provided protocol. Plasma was then collected from the remaining blood sample by low-speed centrifugation. Total RNA was then purified from 200 μL of the human plasma using Norgen's Total RNA Purification Kit (Cat #17200, Norgen, Thorold, Canada) according to the provided protocol.

Next, the hsa-miR-486-5p was depleted from the total RNA samples using the probe described in Example 1. Briefly, Streptavidin Magnetic Beads were prepared by aliquoting 125 μL (500 μg) of Streptavidin Magnetic Beads (New England Biolabs, Whitby, Canada) into a clean RNase-free microcentrifuge tube, and 100 μL of buffer [0.5 M NaCl, 20 mM Tris-HCl (pH 7.5), 1 mM EDTA] was added to the beads and they were then vortexed to suspend. A magnet was then applied to the side of the tube for approximately 30 seconds, and the supernatant was removed and discarded. Next, 1.0 $A_{260}$ unit of the biotin-(hsa-miR-486-5p capture probe) was dissolved in 500 μL of buffer [0.5 M NaCl, 20 mM Tris-HCl (pH 7.5), 1 mM EDTA] to a final concentration 8 pmol/μL. Next, 25 μL of the biotin-(hsa-miR-486-5p capture probe) solution was added to the prepared magnetic beads and vortexed to suspend beads. This was then incubated at room temperature for 5 minutes with occasional agitation by hand, then a magnet was applied and the supernatant was again removed and discarded. The beads were washed by adding 100 μL of buffer [0.5 M NaCl, 20 mM Tris-HCl (pH 7.5), 1 mM EDTA], vortexing to suspend, and then applying a magnet and discarding the supernatant. The beads were then washed a second time in the same manner.

Next, 25 μL of each total RNA preparation purified from the blood and plasma samples was mixed with 25 μL of buffer [1 M NaCl, 40 mM Tris-HCl (pH 7.5), 2 mM EDTA] and heated at 65° C. for 5 minutes then quickly chilled at 4° C. for 3 minutes. The total RNA sample was then added to the previously prepared magnetic beads. The mixture was vortexed to suspend the particles, then incubated at room temperature for 10 minutes with occasional agitation by hand. A magnet was then applied and the supernatant (containing the depleted RNA) was collected. Next, 100 μL of the buffer was again added to the beads, followed by vortexing to suspend the beads. Again, a magnet was applied and the supernatant (containing the depleted RNA) was collected. This process was then repeated, for a total of 3 collections of the depleted RNA. Finally, 100 μL of a cold low salt buffer [0.15 M NaCl, 20 mM Tris-HCl (pH 7.5), 1 mM EDTA] was added to beads, and vortexed to suspend. Again, a magnet was applied and the supernatant was removed and collected. All of the recovered supernatants were then pooled.

The hsa-miR-486-5p-depleted RNA can be assayed or further processed (e.g. preparation of a sequencing library)

immediately or it can be purified prior to the assay. Multiple purification and concentration methods are possible, including through the use of silicon carbide columns, silica columns, gel electrophoresis or ethanol precipitation.

Example 6—Improved Ratio of Useful Data Obtained During Small RNA Next Generation Sequencing of Human Blood and Plasma by Selectively Depleting the Highly Abundant hsa-miR-486-5p Three mL blood samples were collected into 2 Tempus™ Blood RNA Tubes (Applied Biosystems, Foster City, United States) from two different healthy donors (Donor 1 and Donor 2). Total RNA was then purified from the tubes using Norgen's Preserved Blood RNA Purification Kit I (for use with Tempus™ Blood RNA Tubes) (Cat #43400, Norgen, Thorold, Canada) according to the provided protocol. A 2.5 mL blood sample was collected into a Paxgene® Blood RNA Tubes (BD Biosciences, Mississauga, Canada) from a healthy donor (Donor 1). Total RNA was then purified from the tube using Norgen's Preserved Blood RNA Purification Kit II (for use with PAXgene™ Blood RNA Tubes) (Cat #43500, Norgen, Thorold, Canada) according to the provided protocol. A 10 mL blood sample was collected into a BD Vacutainer® Venous Blood Collection Tube (18 mg K2 EDTA, Spray-Dried) (BD Diagnostics, Mississauga, Canada) from a single healthy donor (Donor 1). Total RNA was then purified from 100 μL of the whole blood using Norgen's Total RNA Purification Kit (Cat #17200, Norge, Thorold, Canada) according to the provided protocol. Plasma was then collected from the remaining blood sample by low-speed centrifugation. Total RNA was then purified from 200 μL of the human plasma sample using Norgen's Total RNA Purification Kit (Cat #17200, Norgen, Thorold, Canada) according to the provided protocol. Next, the total RNA samples purified from each condition (Tempus™ 1, Tempus™ 2, PAXgene™, whole blood and plasma) were divided in half. The hsa-miR-486-5p fragment was depleted from half of each of the divided samples as described in Example 4 and using the method outlined in Example 5. The other half of each RNA sample was not depleted and therefore was used as the control.

The five different samples of hsa-miR-486-5p-depleted RNA from were then concentrated using Norgen's Plasma/Serum RNA Isolation Mini Kit (Cat #55000, Norgen, Thorold, Canada) with a slight modification to the first two steps in the provided protocol: 1) the hsa-miR-486-5p-depleted RNA was mixed with an equal volume of Lysis Buffer A; and 2) the resulting mixture was then mixed with an equal volume of 96-100% ethanol (for example, a 350 μL RNA sample depleted of hsa-miR-486-5p was first mixed with 350 μL of Lysis Buffer A and then mixed with 700 μL of 96-100% ethanol). Subsequently, the provided protocol was followed as specified in the kit insert of Norgen's Plasma/Serum RNA Isolation Mini Kit (Cat #55000, Norgen, Thorold, Canada), starting with Step 3.

The concentrated hsa-miR-486-5p-depleted RNA from each donor was then used for small RNA library preparation for downstream NGS analysis. Briefly, using Norgen's Small RNA Library Preparation Kit for Illumina (Cat #63600, Norgen, Thorold, Canada), the RNA was first ligated to the 3' adapter, followed by 3' adaptor removal. Next, the 5' adapter was ligated to the 5' end of the RNA, which was then reverse transcribed into cDNA. This was followed by a limited (15) cycle PCR amplification to enrich the cDNA and also to attach the indexing (barcode) sequences. The indexed libraries were then resolved on a 6% TBE gel and the fragments of interest excised from the gel, crushed and left over-night in 200 μL of water to release DNA. The crushed gel pieces were filtered out and the DNA in the filtrate concentrated using Norgen's RNA Clean-Up and Concentration Micro-Elute Kit (Cat #61000, Norgen, Thorold, Canada) according to the provided protocol. All libraries were quantified and assessed for library size by the Agilent Bioanalyzer using the Agilent High Sensitivity DNA Kit (Agilent Technologies, Santa Clara, United States). As a control, the RNA isolated from each condition that was not depleted of hsa-miR-486-5p was also used for small RNA library preparation.

Next, all 10 of the small RNA libraries were sequenced on the Illumina MiSeq® (Illumina Inc., San Diego, United States) instrument according to the instructions provided by the manufacturer (Preparing Libraries for Sequencing on the MiSeq® and the MiSeq® System User Guide). The resulting NGS sequencing data was then analyzed in a number of different ways to verify that the ratio of useful data obtained was improved in the small RNA libraries prepared from the blood and plasma that was depleted of hsa-miR-486-5p compared to the control small RNA libraries prepared from non-depleted blood and plasma.

First, the overall number of raw NGS reads mapping to miR-486-5p was determined for the control (non-depleted) and the miR-486-5p-depleted RNA, and the results are shown in Table 2. As it can be seen, the non-depleted control samples result in hundreds of thousands of reads that map to miR-486-5p, while the miR-486-5p-depleted RNA resulted in minimum 70 times or more reduction of reads that map to miR-486-5p. Therefore, the miR-486-5p transcript has been successfully removed from the samples, and the resources in the NGS run can now be used to map and sequence the less abundant miRNA molecules that are present.

TABLE 2

| | Tempus | | | | Paxgene | | Whole Blood | | Plasma | |
|---|---|---|---|---|---|---|---|---|---|---|
| | Control (Non-Depleted) RNA | | miR-486-5p-depleted RNA | | Control (Non-Depleted) RNA | miR-486-5p-depleted RNA | Control (Non-Depleted) RNA | miR-486-5p-depleted RNA | Control (Non-Depleted) RNA | miR-486-5p-depleted RNA |
| | Donor 1 | Donor 2 | Donor 1 | Donor 2 | | | | | | |
| Number of Reads Mapping to miR-486-5p | 842639 | 871475 | 3159 | 12344 | 666264 | 3948 | 501556 | 1869 | 18174 | 186 |

Figure 5:
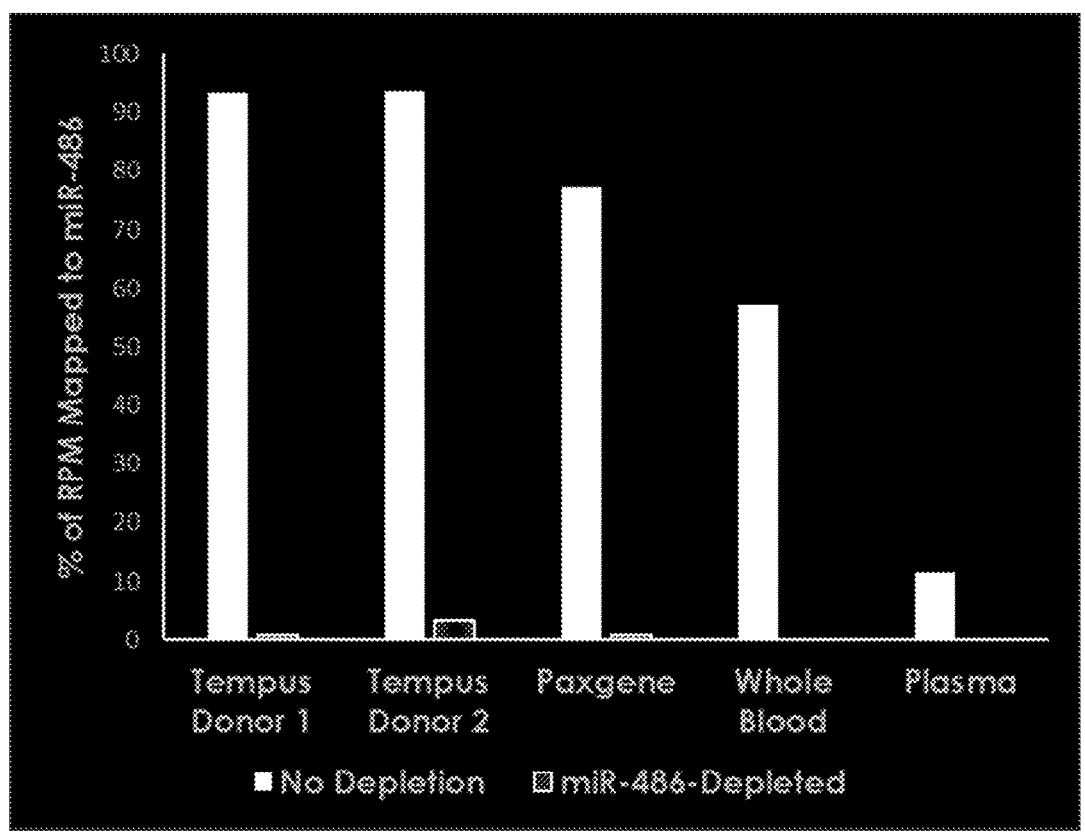
FIG. 5 is a graph depicting the percentage of all reads in next generation sequencing (NGS) runs that map to miRNA from both control (non-depleted) RNA samples and from miR-486-5p-depleted RNA samples isolated from blood collected on Tempus™ tubes from Donor 1 and 2, from RNA samples isolated from blood collected on Paxgene® tubes from a single donor, from RNA isolated from whole blood from a single donor and RNA isolated from plasma samples from a single donor.

FIG. 5 is a graph depicting the percent of all miRNA reads in an NGS run that map to miR-486-5p from both the control (non-depleted) samples, as well as the miR-486-5p-depleted samples. For Tempus™ RNA collected from Donor 1, the control sample showed 93.3% of miRNA reads mapping to miR-486-5p, while the miR-486-5p-depleted sample showed 0.6% of reads mapping to miR-486-5p. For Tempus™ RNA collected from Donor 2, the control sample showed 93.4% of miRNA reads mapping to miR-486-5p, while the miR-486-5p-depleted sample showed 3.2% of reads mapping to miR-486-5p. For Paxgene® RNA, the control sample showed 77.2% of miRNA reads mapping to miR-486-5p, while the miR-486-5p-depleted sample showed 0.8% of reads mapping to miR-486-5p. For Whole Blood RNA, the control sample showed 57.0% of miRNA reads mapping to miR-486-5p, while the miR-486-5p-depleted sample showed 0.3% of reads mapping to miR-486-5p. For Plasma RNA, the control sample showed 11.4% of miRNA reads mapping to miR-486-5p, while the miR-486-5p-depleted sample showed 0.1% of reads mapping to miR-486-5p. Therefore, miR-486-5p-depletion resulted in significantly more reads that can be mapped to the other miRNA inserts that may be otherwise masked by the overwhelming presence of miR-486-5p, and thus the ratio of useful data obtained during small RNA next generation sequencing of human blood or plasma is greatly improved.

Figure 6:
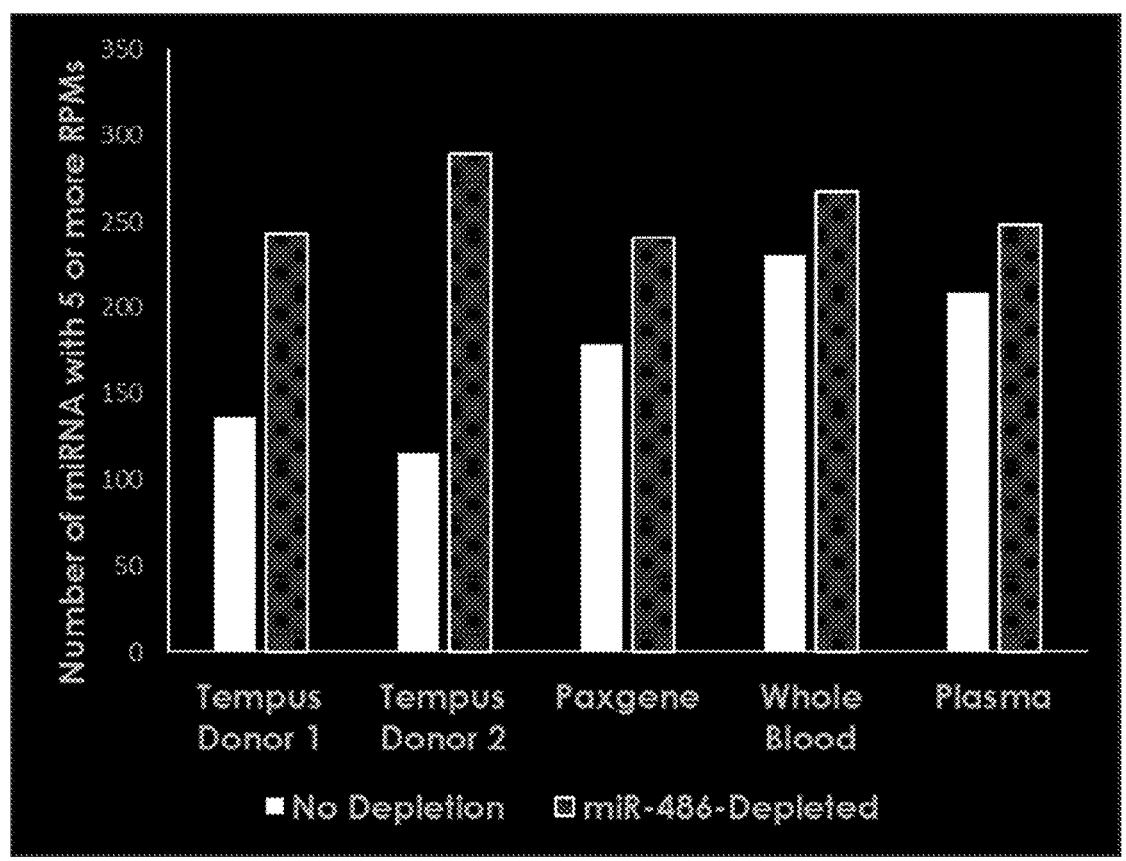
FIG. 6 is a graph depicting the number of miRNA detected in NGS runs from libraries created from both control (non-depleted) RNA samples and from miR-486-5p-depleted RNA samples isolated from blood collected on Tempus tubes from Donor 1 and 2, from RNA samples isolated from blood collected on Paxgene tubes from a single donor, from RNA isolated from whole blood from a single donor and RNA isolated from plasma samples from a single donor.

FIG. 6 is a graph depicting the number of miRNA detected in NGS runs from libraries created from both the control (non-depleted) samples, as well as the miR-486-5p-depleted samples. For Tempus™ RNA collected from Donor 1, the control sample showed 136 miRNAs, while the miR-486-5p-depleted sample showed 243 miRNA inserts. For Tempus™ RNA collected from Donor 2, the control sample showed 115 miRNAs, while the miR-486-5p-depleted sample showed 289 miRNA inserts. For Paxgene® RNA, the control sample showed 179 miRNAs, while miR-486-5p-depleted sample showed 240 miRNA inserts. For Whole Blood RNA, the control sample showed 230 miRNAs, while miR-486-5p-depleted sample showed 267 miRNA inserts. For Plasma RNA, the control sample showed 209 miRNAs, while miR-486-5p-depleted sample showed 248 miRNA inserts. Therefore, miR-486-5p-depletion resulted in a greater sensitivity of miRNA detection in all samples because of increased sequencing depth. These results indicate that, in some blood samples, close to double the amount of miRNAs can be reliably called in miR-486-5p-depleted RNA vs. control (non-depleted) RNA, therefore demonstrating that the method of the present invention improves the signal-to-noise ratio and allows for more low-abundance miRNAs to be detected during NGS applications.

REFERENCES

Brenu E W, Ashton K J, Batovska J, Staines D R, Marshall-Gradisnik S M. "*High-throughput sequencing of plasma microRNA in chronic fatigue syndrome/myalgic encephalomyelitis*". PLoS One. 2014 Sep. 19; 9(9):e102783.

Dhahbi J M, Spindler S R, Atamna H, Boffelli D, Mote P, Martin D I. "*5'-YRNA fragments derived by processing of transcripts from specific YRNA genes and pseudogenes are abundant in human serum and plasma*". Physiol Genomics. 2013 Nov. 1; 45(21):990-8.

Song L, Lin C, Gong H, Wang C, Liu L, Wu J, Tao S, Hu B, Cheng S Y, Li M, and Li J. "*miR-486 sustains NF-κB activity by disrupting multiple NF-KB-negative feedback loops*". Cell Research. 2012 Dec. 18; 23:274-289.

Chen H, Ren C, Han C, Wang D, Chen Y, and Fu D. "*Expression and Prognostic Value of miR-486-5p in Patients with Gastric Adenocarcinoma.*" PLoS One. 2015 Mar. 20; 10(3): e0119384.

Tonge D P and Gant T W. "*What is normal? Next generation sequencing-driven analysis of the human circulating miRNAome.*" BMC Molecular Biology. 2016 Feb. 9; 17:4.

The invention claimed is:

1. A method of improving global gene expression analysis for a population of small RNA molecules derived from human blood, plasma and/or serum, the method comprising the step of depleting 5'-RNAY4 fragments and/or miR-486-5p fragments from the population of small RNA molecules, wherein the step of depleting 5'-RNAY4 fragments and/or miR-486-5p fragments from the population of small RNA molecules comprises:

adding 5'-RNAY4 specific oligonucleotide probes and/or miR-486-5p specific oligonucleotide probes to a sample containing the population of small RNA molecules, wherein each 5'-RNAY4 specific oligonucleotide probe comprises a nucleotide sequence that is the complement to a nucleotide sequence of the 5' end of RNAY4 and each miR-486-5p specific oligonucleotide probes comprises a nucleotide sequence that is the complement to a nucleotide sequence of miR-486-5p;

forming a complex between one or more 5'-RNAY4 fragments and a 5'-RNAY4 specific oligonucleotide probe and/or forming a complex between one or more miR-486-5p fragments and a miR-486-5p specific oligonucleotide probe; and removing the 5'-RNAY4:oligonucleotide complexes and/or the miR-486-5p:oligonucleotide complexes from the sample, wherein the remaining sample contains a 5'-RNAY4 and/or miR-486-5p depleted population of small RNA molecules;

wherein the step of removing the 5'-RNAY4:oligonucleotide complexes and/or miR-486-5p:oligonucleotide complexes from the sample comprises:

combining the sample with a binding buffer, an alcohol and a silicon carbide slurry to provide a binding mixture, wherein the alcohol concentration of the binding mixture is about 1-30% (v/v) to affect selective binding of the 5'-RNAY4:oligonucleotide complexes and/or miR-486-5p:oligonucleotide complexes to the silicon carbide;

removing the 5'-RNAY4:oligonucleotide complex and/or miR-486-5p:oligonucleotide complex bound SiC from the sample; and collecting the remaining sample containing the 5'-RNAY4 and/or miR-486-5p depleted population of small RNA molecules.

2. A method of improving global gene expression analysis for a population of small RNA molecules derived from human blood, plasma and/or serum, the method comprising the step of depleting 5'-RNAY4 fragments and/or miR-486-5p fragments from the population of small RNA molecules, wherein the step of depleting 5'-RNAY4 fragments and/or miR-486-5p fragments from the population of small RNA molecules comprises:

adding 5'-RNAY4 specific oligonucleotide probes and/or miR-486-5p specific oligonucleotide probes to a sample containing the population of small RNA molecules, wherein each 5'-RNAY4 specific oligonucleotide probe comprises a nucleotide sequence that is the complement to a nucleotide sequence of the 5' end of RNAY4 and each miR-486-5p specific oligonucleotide probes comprises a nucleotide sequence that is the complement to a nucleotide sequence of miR-486-5p;

forming a complex between one or more 5'-RNAY4 fragments and a 5'-RNAY4 specific oligonucleotide probe and/or forming a complex between one or more miR-486-5p fragments and a miR-486-5p specific oligonucleotide probe; and removing the 5'-RNAY4:oligonucleotide complexes and/or the miR-486-5p:oligonucleotide complexes from the sample, wherein the remaining sample contains a 5'-RNAY4 and/or miR-486-5p depleted population of small RNA molecules;

wherein the step of removing the 5'-RNAY4:oligonucleotide complexes and/or miR-486-5p:oligonucleotide complexes comprises:

combining the sample with a binding buffer and alcohol to provide a binding mixture;

applying the binding mixture to a silicon carbide column, wherein the alcohol concentration of the binding mixture is about 1-30% (v/v) to affect selective binding of the 5'-RNAY4:oligonucleotide complexes and/or miR-486-5p:oligonucleotide complexes to the silicon carbide;

collecting the column flowthrough containing the 5'-RNAY4 and/or miR-486-5p depleted population of small RNA molecules.

3. The method of claim 1, wherein the alcohol is ethanol and the alcohol concentration of the binding mixture is about 1-10% (v/v).

4. The method of claim 2, wherein the alcohol is ethanol and the alcohol concentration of the binding mixture is about 1-10% (v/v).

* * * * *

SEQUENCE LISTING

```
<160> NUMBER OF SEQ ID NOS: 4

<210> SEQ ID NO 1
<211> LENGTH: 32
<212> TYPE: RNA
<213> ORGANISM: Artificial Sequence
<220> FEATURE:
<223> OTHER INFORMATION: 5'-RNAY4 fragment

<400> SEQUENCE: 1
ggcugguccg augguagugg guuaucagaa cu                                    32

<210> SEQ ID NO 2
<211> LENGTH: 32
<212> TYPE: DNA
<213> ORGANISM: Artificial Sequence
<220> FEATURE:
<223> OTHER INFORMATION: 5'-RNAY4 fragment capture probe

<400> SEQUENCE: 2
agttctgata acccactacc atcggaccag cc                                    32

<210> SEQ ID NO 3
<211> LENGTH: 22
<212> TYPE: RNA
<213> ORGANISM: Artificial Sequence
<220> FEATURE:
<223> OTHER INFORMATION: miR-486-5p fragment

<400> SEQUENCE: 3
```

```
uccuguacug agcugccccg ag                                              22

<210> SEQ ID NO 4
<211> LENGTH: 22
<212> TYPE: DNA
<213> ORGANISM: Artificial Sequence
<220> FEATURE:
<223> OTHER INFORMATION: miR-486-5p capture probe

<400> SEQUENCE: 4
ctcggggcag ctcagtacag ga                                              22
```